(12) United States Patent
Yang et al.

(10) Patent No.: US 12,336,786 B2
(45) Date of Patent: Jun. 24, 2025

(54) PHOTOACOUSTIC IMAGING SYSTEM, AND LASER ENERGY CORRECTION METHOD AND PROMPTING METHOD THEREFOR

(71) Applicant: SHENZHEN MINDRAY BIO-MEDICAL ELECTRONICS CO., LTD., Guangdong (CN)

(72) Inventors: Fang Yang, Shenzhen (CN); Xujin He, Shenzhen (CN); Lei Zhu, Shenzhen (CN); Xiaoyun Chang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 188 days.

(21) Appl. No.: 18/078,858

(22) Filed: Dec. 9, 2022

(65) Prior Publication Data
US 2023/0181044 A1    Jun. 15, 2023

(30) Foreign Application Priority Data
Dec. 9, 2021   (CN) .......................... 202111498408.2

(51) Int. Cl.
A61B 5/00     (2006.01)
(52) U.S. Cl.
CPC .......... A61B 5/0095 (2013.01); A61B 5/7235 (2013.01); A61B 5/7425 (2013.01);
(Continued)
(58) Field of Classification Search
CPC ... A61B 5/0095; A61B 5/7235; A61B 5/7425; A61B 2560/0223; A61B 2562/0204
See application file for complete search history.

(56) References Cited

U.S. PATENT DOCUMENTS

| | | | |
|---|---|---|---|
| 9,920,188 B2* | 3/2018 | Vogt | C08K 3/22 |
| 2013/0109941 A1* | 5/2013 | Li | G01N 21/49 |
| | | | 600/407 |

(Continued)

*Primary Examiner* — Dixomara Vargas
(74) *Attorney, Agent, or Firm* — Sheppard Mullin Richter & Hampton LLP

(57) ABSTRACT

Disclosed are photoacoustic imaging systems, and laser energy correction methods and prompting methods therefor, and photoacoustic imaging systems. The method includes: controlling a laser to transmit a first optical pulse to a target tissue; receiving a first acoustic wave generated by the target tissue absorbing the first optical pulse to acquire a first photoacoustic signal, and receiving a third acoustic wave generated by a marker absorbing the first optical pulse to acquire a third photoacoustic signal; controlling the laser to transmit a second optical pulse to the target tissue; receiving a second acoustic wave generated by the target tissue, and receiving a fourth acoustic wave generated by the marker; correcting a signal intensity of the first photoacoustic signal based on a signal intensity of the third photoacoustic signal together with a first absorption coefficient of the marker with respect to the first optical pulse, and correcting a signal intensity of the second photoacoustic signal based on the fourth photoacoustic signal together with a second absorption coefficient of the marker with respect to the second optical pulse; and acquiring an oxygen saturation of the target tissue based on the corrected signal intensity of the first photoacoustic signal and the corrected signal intensity of the second photoacoustic signal.

20 Claims, 7 Drawing Sheets

(52) U.S. Cl.
CPC ................ *A61B 2560/0223* (2013.01); *A61B 2562/0204* (2013.01)

(56) References Cited

U.S. PATENT DOCUMENTS

| | | | | |
|---|---|---|---|---|
| 2013/0109949 A1* | 5/2013 | Li | ................ | G01N 21/4738 600/407 |
| 2015/0101411 A1* | 4/2015 | Zalev | ................ | A61B 5/0095 73/643 |

* cited by examiner

PHOTOACOUSTIC IMAGING SYSTEM, AND LASER ENERGY CORRECTION METHOD AND PROMPTING METHOD THEREFOR

CROSS-REFERENCE TO RELATED APPLICATIONS

This application is based on and claims priority to and benefits of Chinese Patent Application No. 202111498408.2, filed on Dec. 9, 2021. The entire content of the above-referenced application is incorporated herein by reference.

TECHNICAL FIELD

The present application generally relates to medical equipment, and more particularly to laser energy correction methods and prompting methods in photoacoustic imaging systems, and photoacoustic imaging systems.

BACKGROUND OF THE INVENTION

Photoacoustic imaging system is a new non-destructive biomedical detection technology, which uses a pulsed laser as an excitation source to irradiate and enable biological tissue to absorb light energy to generate an ultrasonic wave (i.e. a photoacoustic signal), and then use a detector to receive the photoacoustic signals. Oxygen saturation ($SaO_2$) is an important physiological indicator in clinical diagnosis, which refers to the percentage of the volume of oxy-hemoglobin in the blood to the total bindable hemoglobin, that is, the concentration of blood oxygen in the blood. The oxygen saturation can be detected via a photoacoustic imaging system.

However, during the usage of the photoacoustic imaging system, due to the performance limitation of the laser, the energy of each laser pulse emitted is not completely equal; sometimes, there is even a large deviation. The consequence of energy instability is that a jump in intensity may occur in each frame of photoacoustic image. The accuracy of calculating the oxygen saturation depends very much on the accuracy and stability of the intensity of the photoacoustic image. At the same time, for safety reasons, when the laser is abnormal and radiates laser energy higher than a safety standard, it may cause damage to a measured tissue.

SUMMARY OF THE INVENTION

The present application is proposed to solve at least one of the above problems. Specifically, A laser energy correction method in a photoacoustic imaging system is provided in a first aspect of the present application. The method may include: controlling a laser to transmit a first optical pulse to a target tissue; receiving a first acoustic wave generated by the target tissue absorbing the first optical pulse to acquire a first photoacoustic signal, and receiving a third acoustic wave generated by a marker absorbing the first optical pulse to acquire a third photoacoustic signal; controlling the laser to transmit a second optical pulse to the target tissue, the first optical pulse having a first wavelength and the second optical pulse having a second wavelength different from the first wavelength; receiving a second acoustic wave generated by the target tissue absorbing the second optical pulse to acquire a second photoacoustic signal, and receiving a fourth acoustic wave generated by the marker absorbing the second optical pulse to acquire a fourth photoacoustic signal; correcting a signal intensity of the first photoacoustic signal based on a signal intensity of the third photoacoustic signal together with a first absorption coefficient of the marker with respect to the first optical pulse, and correcting a signal intensity of the second photoacoustic signal based on the fourth photoacoustic signal together with a second absorption coefficient of the marker with respect to the second optical pulse; and acquiring an oxygen saturation of the target tissue based on the corrected signal intensity of the first photoacoustic signal and the corrected signal intensity of the second photoacoustic signal.

A laser energy correction method in a photoacoustic imaging system is provided in a second aspect of the present application. The method may include: controlling a laser to transmit a first optical pulse to a target tissue; receiving a first acoustic wave generated by the target tissue absorbing the first optical pulse to acquire a first photoacoustic signal, and receiving a third acoustic wave generated by a marker absorbing the first optical pulse to acquire a third photoacoustic signal; acquiring a first photoacoustic image based on the first photoacoustic signal and the third photoacoustic signal; controlling the laser to transmit a second optical pulse to the target tissue; receiving a second acoustic wave generated by the target tissue absorbing the second optical pulse to acquire a second photoacoustic signal, and receiving a fourth acoustic wave generated by the marker absorbing the second optical pulse to acquire a fourth photoacoustic signal; acquiring a second photoacoustic image based on the second photoacoustic signal and the fourth photoacoustic signal; acquiring a first brightness value of a region corresponding to at least part of the marker in the first photoacoustic image, and acquiring a second brightness value of the region corresponding to at least part of the marker in the second photoacoustic image; correcting a signal intensity of the first photoacoustic signal based on the first brightness value together with a first absorption coefficient of the marker with respect to the first optical pulse, and correcting a signal intensity of the second photoacoustic signal based on the second brightness value together with a second absorption coefficient of the marker with respect to the second optical pulse; and acquiring an oxygen saturation of the target tissue based on the corrected signal intensity of the first photoacoustic signal and the corrected signal intensity of the second photoacoustic signal.

A laser energy prompting method in a photoacoustic imaging system is provided in a third aspect of the present application. The method may include: controlling a laser to transmit a first optical pulse to a target tissue; receiving a first acoustic wave generated by the target tissue absorbing the first optical pulse to acquire a first photoacoustic signal, and receiving a third acoustic wave generated by the marker absorbing the first optical pulse to acquire a third photoacoustic signal; and comparing a signal intensity of the third photoacoustic signal with a first preset threshold range, and outputting prompt information and/or controlling to turn off the laser when the signal intensity of the third photoacoustic signal exceeds the first preset threshold range.

A laser energy prompting method in a photoacoustic imaging system is provided in a fourth aspect of the present application. The method may include: controlling a laser to transmit a first optical pulse to a target tissue; receiving a first acoustic wave generated by the target tissue absorbing the first optical pulse to acquire a first photoacoustic signal, and receiving a third acoustic wave generated by a marker absorbing the first optical pulse to acquire a third photoacoustic signal; acquiring a first photoacoustic image based on the first photoacoustic signal and the third photoacoustic signal; acquiring a first brightness value of at least part of the marker in the first photoacoustic image; and comparing the first brightness value with a first preset brightness range, and outputting prompting information and/or controlling to turn off the laser when the first brightness value exceeds the first preset brightness range.

A photoacoustic imaging system is provided in a fifth aspect of the present application. The system may include:
an ultrasonic probe;
a laser configured to transmit a first optical pulse and a second optical pulse to a target tissue, the first optical pulse having a first wavelength and the second optical pulse having a second wavelength;
a receiving circuit configured to control the ultrasonic probe to receive a first acoustic wave generated by the target tissue absorbing the first optical pulse to acquire a first photoacoustic signal, control the ultrasonic probe to receive a second acoustic wave generated by the target tissue absorbing the second optical pulse to acquire a second photoacoustic signal, control the ultrasonic probe to receive a third acoustic wave generated by the marker absorbing the first optical pulse to acquire a third photoacoustic signal, and receive a fourth acoustic wave generated by the marker absorbing the second optical pulse to acquire a fourth photoacoustic signal;
a memory configured to store executable program instructions;
a processor configured to execute the program instructions stored in the memory, so that the processor executes the method mentioned above; and
a display configured to display visual information.

With the laser energy correction method disclosed in the first aspect of the present application, by correcting the photoacoustic signal generated by a laser source irradiating the target tissue with the photoacoustic signal generated by the laser source irradiating the marker, and by acquiring the oxygen saturation of the target tissue based on the corrected photoacoustic signal, laser emission energy can accordingly be calibrated to be consistent, the accuracy of the oxygen saturation can be improved, and the method according to the present application is less costly than the method of adding hardware.

With the laser energy correction method disclosed in the second aspect of the present application, by acquiring a brightness value of the marker in the photoacoustic image to use the brightness value to correct a corresponding photoacoustic signal, and by acquiring the oxygen saturation of the target tissue based on the corrected first photoacoustic signal and the corrected second photoacoustic signal, the accuracy of oxygen saturation can be improved, and the method according to the present application is less costly than the method of adding hardware.

With the laser energy prompting method disclosed in the third aspect of the present application, by comparing the third photoacoustic signal with the first preset threshold range, and outputting prompt information and/or controlling to turn off the laser source when the signal intensity of the third photoacoustic signal exceeds the first preset threshold range, damage to the target tissue caused by the energy of the first optical pulse transmitted by the light source exceeding a safety range can be avoided, thereby improving the safety and reliability of the photoacoustic imaging system.

With the laser energy prompting method disclosed in the fourth aspect of the present application, by acquiring the first brightness value of at least part of the marker in the first photoacoustic image, comparing the first brightness value with the first preset brightness range, and outputting prompting information and/or controlling to turn off the laser when the first brightness value exceeds the first preset brightness range, damage to the target tissue caused by the energy of the first optical pulse transmitted by the laser exceeding a safety range can be avoided, thereby improving the safety and reliability of the photoacoustic imaging system.

BRIEF DESCRIPTION OF THE DRAWINGS

In order to illustrate the technical solutions in the embodiments of the present invention more clearly, the following briefly introduces the accompanying drawings used in the description of the embodiments. Obviously, the accompanying drawings in the following description are only some embodiments of the present invention. For those of ordinary skill in the art, other drawings can also be obtained from these drawings without creative labor.

DETAILED DESCRIPTION OF EMBODIMENTS

Figure 1:
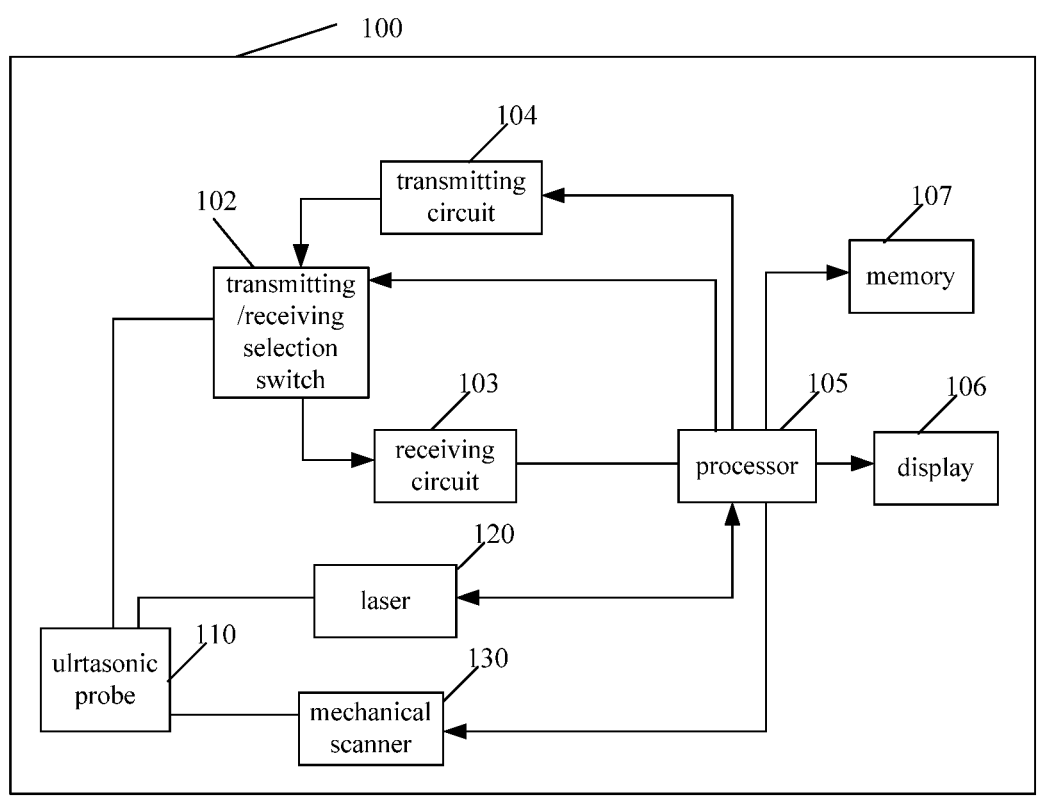
FIG. 1 is a schematic block diagram of a photoacoustic imaging system in an embodiment of the present application.

In order to make the objectives, technical solutions, and advantages of the present application more clearly, example embodiments according to the present application will be described in detail below with reference to the accompanying drawings. Apparently, the described embodiments are merely some rather than all of the embodiments of the present application. It should be understood that the example embodiments described herein do not constitute any limitation to the present application. All other embodiments derived by those skilled in the art without creative efforts on the basis of the embodiments of the present application described in the present application shall fall within the scope of protection of the present application.

In the following description, a large number of specific details are given to provide a more thorough understanding of the present application. However, it would be understood by those skilled in the art that the present application can be implemented without one or more of these details. In other examples, to avoid confusion with the present application, some technical features known in the art are not described.

It should be understood that the present application can be implemented in different forms and should not be construed as being limited to the embodiments presented herein. On the contrary, these embodiments are provided to make the disclosure thorough and complete, and to fully convey the scope of the present application to those skilled in the art.

The terms used herein are intended only to describe specific embodiments and do not constitute a limitation to the present application. When used herein, the singular forms of "a", "an", and "said/the" are also intended to include plural forms, unless the context clearly indicates otherwise. It should also be appreciated that the terms "comprise" and/or "include", when used in the specification, determine the existence of described features, integers, steps, operations, elements, and/or units, but do not exclude the existence or addition of one or more other features, integers, steps, operations, elements, units, and/or groups thereof. As used herein, the term "and/or" includes any and all combinations of relevant listed items.

For a thorough understanding of the present application, detailed steps and detailed structures will be provided in the following description to explain the technical solutions proposed by the present application. The preferred embodiments of the present application are described in detail as follows. However, in addition to these detailed descriptions, the present application may further have other implementations.

Specifically, the photoacoustic imaging systems, the laser energy correction methods and the prompting methods according to the present application are described in detail below with reference to the accompanying drawings. The features of the embodiments and implementations described below may be combined with each other without conflict.

FIG. 1 schematically shows a structural block diagram of a photoacoustic imaging system 10 in an embodiment of the present application. The photoacoustic imaging system 10 may include an ultrasonic probe 110, a laser 120 and a mechanical scanner 130, and a transmitting circuit 101, a transmitting/receiving selection switch 102, a receiving circuit 103, a processor 105, a display 106, and a memory 107. The photoacoustic imaging system 10 may certainly also include other equipment or devices that are not shown in the figures.

The transmitting circuit 101 can excite the ultrasonic probe 110 to transmit ultrasonic waves to a target tissue. After the ultrasonic probe 110 transmits ultrasonic waves, the receiving circuit 103 may receive ultrasonic echoes from the target tissue via the ultrasonic probe 110 to obtain ultrasonic echo signals/data The ultrasonic echo signals/data may be sent to the processor 105 directly, or they/it may be performed with beam synthesis processing in a beam synthesis circuit before being sent to the processor 105. The processor 105 may process the ultrasonic echo signals/data to obtain an ultrasound image of the target tissue. The ultrasound image obtained by the processor 105 may be stored in the memory 107. The laser 120 can generate light, which is coupled to the probe via an optical fiber bundle. The light, such as laser pulses, may be transmitted to the target tissue via the optical fiber bundle coupled on the ultrasound probe 110. After transmitting the laser pulses to the target tissue, the receiving circuit 103 may also receive acoustic waves returned by the target tissue under the excitation of the laser via the ultrasonic probe 110 to obtain the photoacoustic signals/data. The photoacoustic signals/data may be sent to the processor 105 directly or after being processed, and be processed by the processor to obtain a photoacoustic image of the target tissue. The mechanical scanner 130 may drive the ultrasonic probe 110 to move. The aforementioned ultrasound image and photoacoustic image may be displayed on the display 106.

It should be noted that in the present application, the ultrasonic probe 110 transmitting the light to the target tissue may specifically refer to transmitting the light to the target tissue via the optical fiber bundle coupled to the ultrasonic probe 110. The optical fiber bundle may be arranged outside the ultrasonic probe 110 or inside the ultrasonic probe 110, which may be adjusted according to actual scenes and is not limited here.

Figure 2:
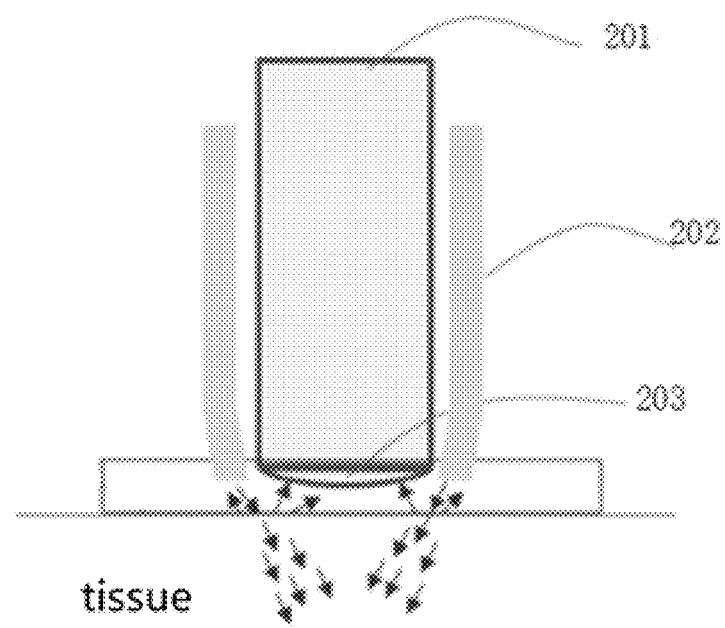
FIG. 2 is a schematic block diagram of a compounded photoacoustic probe in an embodiment of the present application.

In an embodiment, the ultrasonic probe may be implemented as a compounded photoacoustic probe as shown in FIG. 2. The compounded photoacoustic probe may include an ultrasonic probe 201, an optical fiber bundle 202 and an acoustic lens 203. The optical fiber bundle 202 may be coupled to a side of the ultrasonic probe, and the light pulses generated by the laser may be coupled to the compounded photoacoustic probe via the optical fiber bundle, so that the light is irradiated to the surface of the tissue, wherein most of the light beam is radiated into the tissue along the transmitting direction, and a part of it is reflected to the acoustic lens 203 via the skin. The acoustic lens may be used to protect an internal circuit structure, focus acoustic waves and signal transmission.

In an embodiment of the present application, the laser 120 may be connected to the transmitting/receiving selection switch 102 which may control the emission of the light. Alternatively, the laser 120 may be directly connected to the ultrasonic probe 110 via a light conduction tool and coupled to the optical fiber bundle on the ultrasonic probe 110 to conduct the light to both sides of the ultrasonic probe 110 with the optical fiber bundle for irradiating the target tissue in a backward-facing lighting manner. In some implementations, both the laser 120 and the optical fiber bundle are coupled into the probe; in this connection, the inside of the probe may also include ultrasonic transducer elements for ultrasonic imaging, so that the probe can be used not only for conventional ultrasonic imaging, but also for photoacoustic imaging, that is, forming a probe integrating ultrasound imaging and photoacoustic imaging.

The mechanical scanner 130 may enable the ultrasonic probe 110 to receive ultrasonic echo signals/data or photoacoustic signals/data from different orientations, and enable the processor 105 to process the received ultrasonic echo signals/data or photoacoustic signals/data to obtain the ultrasound images or the photoacoustic images.

In this connection, the mechanical scanner 130 is an optional device. In some implementations, the mechanical scanner 130 may be coupled into the probe, that is, the probe may integrate the functionality of mechanical scanning.

In an embodiment of the present application, the mechanical scanner 130 may further include a motor controller and a motor. The motor controller may control the motion trajectory, stroke or speed of the motor in the mechanical scanner 130 according to a control signal sent by the processor.

In an embodiment of the present application, the ultrasonic probe 110 may be independently, or be arranged on the mechanical scanner 130 which drives the ultrasonic probe 110 to move.

In an embodiment of the present application, the ultrasonic probe 110 may specifically include an ultrasonic transducer which has functions of transmitting and receiving signals to perform various imaging such as gray-scale imaging and Doppler blood flow imaging. In addition, in some implementations, the optical fiber bundle and the ultrasonic transducer may be coupled and surrounded by a housing to form a probe integrating photoacoustic imaging and ultrasonic imaging; that is, with the probe of this structure, the probe may transmit the light emitted by the laser to the target tissue, and receive the photoacoustic signal formed by the laser excitation from the target tissue. The probe may certainly also be used for conventional ultrasound imaging, that is, transmitting ultrasonic waves to the target tissue and receiving ultrasonic echoes from the target tissue. Of course, the laser and the ultrasonic transducer may also be coupled directly and surrounded entirely or partially by a housing to form a probe integrating photoacoustic imaging and ultrasonic imaging. Such probe may be used for both photoacoustic imaging and ultrasound imaging.

In an embodiment of the present application, the aforementioned display 106 may be a touch display screen, a liquid crystal display screen and the like built into the photoacoustic imaging system; or it may be an independent display device such as a liquid crystal display, a TV, etc., which is independent of the photoacoustic imaging system; or it may be a display screen of an electronic device such as a smartphone, a tablet or the like. The number of the display 106 may be one or more.

The display 106 may display the ultrasound image, the photoacoustic image, or a blood oxygen image, obtained by the processor 105. In addition, the display 106 can also provide users with a graphical interface for human-computer interaction (i.e. human-computer interaction interface) while displaying the ultrasound image. One or more controlled objects may be arranged on the graphical interface to provide users with inputting an operation instruction to control these controlled objects by using the human-computer interaction device, so as to execute corresponding control operation. For example, an icon is displayed on the graphical interface, which can be operated by using the human-computer interaction device to perform specific functions, such as drawing a region of interest box on the ultrasound image.

Optionally, the photoacoustic imaging system 10 may also include other human-computer interaction devices other than the display 106, which are connected to the processor 105. For example, the processor 105 may be connected with the human-computer interaction device via an external input/output port which may be a wireless communication module, a wired communication module, or a combination of the two. The external input/output port may also be implemented based on USB, bus protocols such as CAN, and/or wired network protocols, and the like.

In this respect, the human-computer interaction device may include an input device for detecting a user's input information. The input information may be, for example, a control instruction for the ultrasonic transmission/reception sequence, or may be an operational input instruction for drawing points, lines or boxes on the ultrasound image or the photoacoustic image, or may include other types of instructions. The input device may include one or more of a keyboard, a mouse, a roller, a trackball, a mobile input device (such as a mobile device or a mobile phone with a touch screen, etc.), a multi-function knob, and the like, or a combination thereof. The human-computer interaction device may also include an output device such as a printer.

The memory 107 may be configured to store instructions executed by the processor, the received photoacoustic signals, the photoacoustic images, the ultrasound images, and the like. The memory 107 may be a flash memory card, a solid-state memory, a hard disk, or the like. It may be a volatile memory and/or a non-volatile memory, a removable memory and/or a non-removable memory, and the like.

In an embodiment, the processor 105 may be implemented as software, hardware, firmware, or any combination thereof, which may use a circuit, one or more application specific integrated circuits (ASICs), one or more general-purpose integrated circuits, one or more microprocessors, one or more programmable logic devices, or any combination of the foregoing circuits and/or devices, or other suitable circuits or devices, so that the processor 105 may perform corresponding steps of the methods in the various embodiments herein.

It should be understood that the components included in the photoacoustic imaging system 100 shown in FIG. 1 are only schematic, and it may include more or fewer components, which is not limited in the present application.

When a person is under different physiological conditions the metabolism of various organs and tissues is different, and the need for blood flow is also different. The function of a healthy biological organ may be achieved by the delivery of oxygen to the body through proper blood circulation. The transport of oxygen may be realized with the help of hemoglobin having two forms: oxy-hemoglobin and deoxy-hemoglobin. Oxygen saturation ($SaO_2$) may refer to the percentage of oxy-hemoglobin in the blood to the total bindable hemoglobin, that is, the concentration of blood oxygen in the blood. At present, $SaO_2$ is used to estimate the oxygen-carrying capacity of hemoglobin, and its calculation formula is:

$$SaO_2 = \frac{[HbO_2]}{[HbO_2] + [Hb]} \times 100\% \qquad (1)$$

The oxygen saturation depends on partial pressure of blood oxygen. In a normal human body, arterial oxygen saturation is 93%~98%, and venous oxygen saturation is 70%~75%. In clinical practice, the oxygen content in human blood is evaluated by measuring arterial oxygen saturation. Compared with normal tissues, cancerous tissues usually exhibit the characteristics of "high blood and low oxygen". Dual-wavelength tissue detection technology is to detect and compare blood oxygen contents in diseased tissues and healthy tissues by two specific wavelengths of infrared light according to different absorption characteristics of oxy-hemoglobin and deoxy-hemoglobin in the near-infrared light region, so as to determine whether a tumor is benign or malignant.

Figure 3:
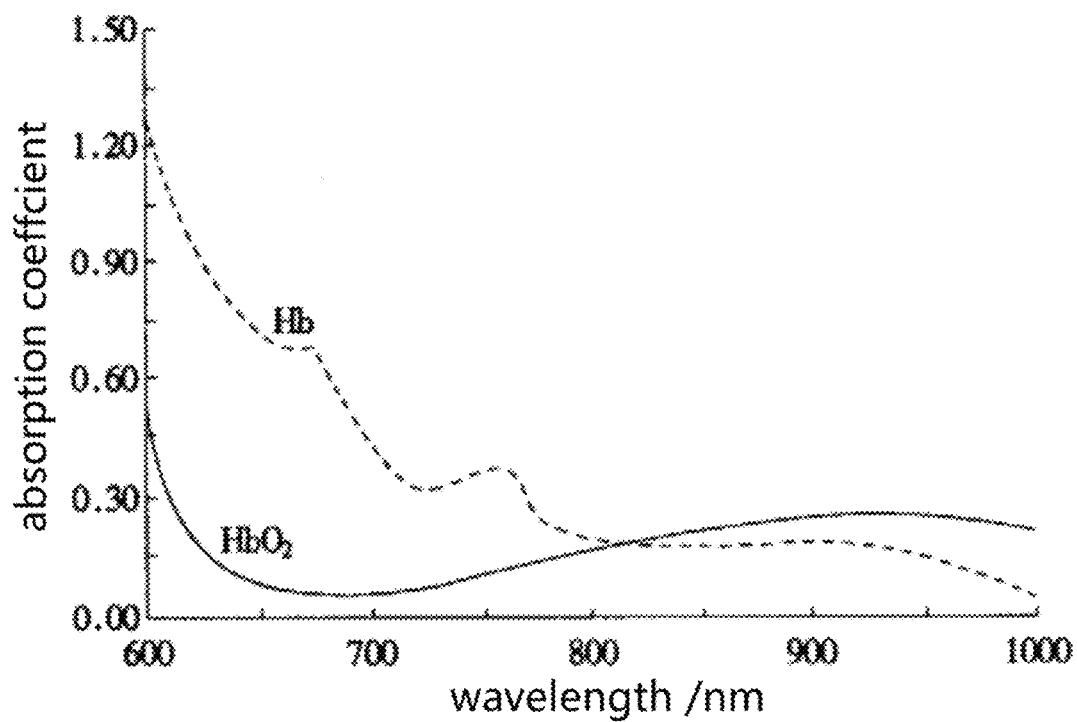
FIG. 3 is an absorption coefficient map of oxy-hemoglobin ($HbO_2$) and deoxy-hemoglobin (Hb) in a near-infrared region.

As shown in FIG. 3, there is an "optical window" in the near-infrared region of 700 nm-900 nm. In this window, the absorption of water is greatly reduced, the tissues mainly rely on the absorption of oxy-hemoglobin ($HbO_2$) and deoxy-hemoglobin (Hb), and the absorption of light mainly reflects the content of $HbO_2$ and Hb. Therefore, the oxygen content in blood can be inferred at this time by detecting the absorption of light by human tissues.

When choosing two light beams with wavelengths in the near-infrared light region (such as $\lambda_1=770$ nm, $\lambda_2=830$ nm) to detect tissues, if only the effects of deoxy hemoglobin (Hb) and oxy hemoglobin ($HbO_2$) are considered, the absorption coefficients at the two wavelengths can be expressed as:

$$\mu_{\lambda_1} = \varepsilon_{Hb}^{\lambda_1} C_{Hb} + \varepsilon_{HbO2}^{\lambda_1} C_{HbO2} \qquad (2)$$

$$\mu_{\lambda_2} = \varepsilon_{Hb}^{\lambda_2} C_{Hb} + \varepsilon_{HbO2}^{\lambda_2} C_{HbO2} \qquad (3)$$

where $C_{Hb}$ and $C_{HbO2}$ represent the contents of Hb and HbO$_2$ respectively, and $\varepsilon_{Hb}^{\lambda_1}$, $\varepsilon_{Hb}^{\lambda_2}$, $\varepsilon_{HbO2}^{\lambda_1}$ and $\varepsilon_{HbO2}^{\lambda_2}$ represent the extinction coefficients of Hb and HbO$_2$ at wavelengths $\lambda_1$ and $\lambda_2$ respectively.

Assuming that the intensity of the photoacoustic signal is proportional to the absorption coefficient of the tissue, the following can be obtained by simplifying the calculation:

$$C_{Hb} = \frac{\varepsilon_{HbO_2}^{\lambda_2} A^{\lambda_1} - \varepsilon_{HbO2}^{\lambda_1} A^{\lambda_2}}{\varepsilon_{Hb}^{\lambda_1}\varepsilon_{HbO2}^{\lambda_2} - \varepsilon_{Hb}^{\lambda_2}\varepsilon_{HbO2}^{\lambda_1}} \quad (4)$$

$$C_{HbO2} = \frac{\varepsilon_{Hb}^{\lambda_1} A^{\lambda_2} - \varepsilon_{Hb}^{\lambda_2} A^{\lambda_1}}{\varepsilon_{Hb}^{\lambda_1}\varepsilon_{HbO2}^{\lambda_2} - \varepsilon_{Hb}^{\lambda_2}\varepsilon_{HbO2}^{\lambda_1}} \quad (5)$$

$$SaO2 = \frac{C_{HbO2}}{C_{Hb} + C_{HbO2}} = \frac{\varepsilon_{Hb}^{\lambda_1} A^{\lambda_2} - \varepsilon_{Hb}^{\lambda_2} A^{\lambda_1}}{A^{\lambda_1}\left(\varepsilon_{HbO2}^{\lambda_2} - \varepsilon_{Hb}^{\lambda_2}\right) + A^{\lambda_2}\left(\varepsilon_{Hb}^{\lambda_1} - \varepsilon_{HbO2}^{\lambda_1}\right)} \times 100\% \quad (6)$$

where $A^{\lambda_1}$ and $A^{\lambda_2}$ represent the intensity information of the photoacoustic signal obtained at the wavelengths $\lambda_1$ and $\lambda_2$, respectively. Meanwhile, $A^{\lambda_1}$ and $A^{\lambda_2}$ are proportional to laser pulse energy $E^{\lambda_1}$ and $E^{\lambda_2}$, respectively. Therefore, when $E^{\lambda_1}$ and $E^{\lambda_2}$ are not equal, the energy of each laser pulse needs to be corrected, so the calculation formula of SaO$_2$ is corrected as follows:

$$SaO2 = \frac{C_{HbO2}}{C_{Hb} + C_{HbO2}} = \frac{\varepsilon_{Hb}^{\lambda_1}\frac{A^{\lambda_2}}{E^{\lambda_2}} - \varepsilon_{Hb}^{\lambda_2}\frac{A^{\lambda_1}}{E^{\lambda_1}}}{\frac{A^{\lambda_1}}{E^{\lambda_1}}\left(\varepsilon_{HbO2}^{\lambda_2} - \varepsilon_{Hb}^{\lambda_2}\right) + \frac{A^{\lambda_2}}{E^{\lambda_2}}\left(\varepsilon_{Hb}^{\lambda_1} - \varepsilon_{HbO2}^{\lambda_1}\right)} \times 100\% \quad (7)$$

In ultrasound imaging, the energy of the acoustic field generated by each emission may be considered to be stable under the condition that the emission voltage is consistent. However, in photoacoustic imaging, due to the performance limitation of the laser, the energy of each laser pulse emitted may be not completely equal, and sometimes there is even a large deviation. The consequence of energy instability is that each frame of photoacoustic image has a jump in intensity, and the accuracy of SaO$_2$ calculation depends very much on the accuracy and stability of the intensity of the photoacoustic image. Meanwhile, for safety reasons, it is necessary to be able to detect the energy of the pulse in real time; in this connection, when the laser is abnormal and radiates a light energy higher than the safety standard, the laser should be stopped immediately to prevent damage to human body.

A commonly used method to solve the above problem is to embed an energy meter inside the laser; however, the embedded energy meter may cause problems as follows: 1. greatly increased cost; 2. the change from the energy measured at the entrance end of the fiber to the energy actually incident into the tissue cannot be considered to be completely linear due to different transmittance of the fiber at different wavelengths; 3. possible large deviation of image result caused by the failure of the energy meter or big error of the output of the energy meter in case of over-reliance on the energy meter; and 4. a potential security risk caused by failure of detection of abnormal laser radiation energy when the energy meter fails.

Figure 4:
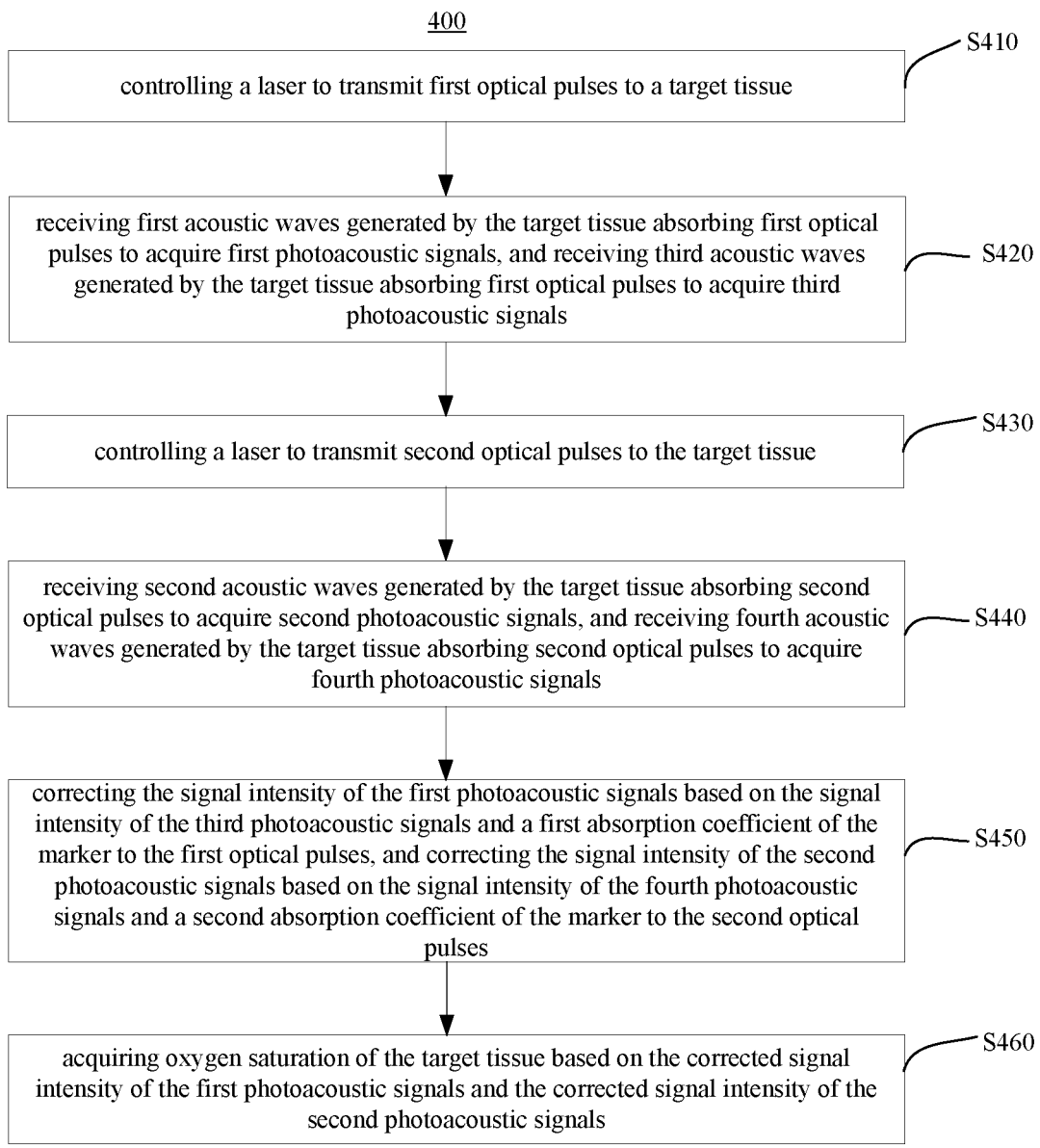
FIG. 4 is a flowchart of a laser energy correction method in a photoacoustic imaging system in an embodiment of the present application.

In view of the existing problems, a laser energy correction method 400 in a photoacoustic imaging system provided in the present application, as shown in FIG. 4, may include the following steps S410 to S460:

Step S410: controlling a laser to transmit a first optical pulse to a target tissue.

The first optical pulse may be transmitted to the target tissue during a first period via an optical fiber bundle coupled on the probe 110. Specifically, a first light may be coupled to the ultrasonic probe via the optical fiber bundle, and then the first optical pulse may be transmitted to the target tissue by the optical fiber bundle coupled on the probe. When the target tissue absorbs the light energy, it will cause heating and thermal expansion, resulting in an acoustic wave (i.e. the photoacoustic signal) propagating outward.

In an embodiment of the present application, the first optical pulse may be generated after the processor 105 sends a first control signal which may include the wavelength, frequency or timing of the first light to the laser 120, and then be coupled to the probe 110 via the optical fiber bundle through which the light is emitted to the target tissue. The position and angle of the emitted light can be controlled by controlling the movement of the probe. When the target tissue absorbs the light energy, it will cause temperature rise and thermal expansion, resulting in a photoacoustic signal that propagates outward.

Step S420: receiving a first acoustic wave generated by the target tissue absorbing the first optical pulse to acquire a first photoacoustic signal, and receiving a third acoustic wave generated by the marker absorbing the first optical pulse to acquire a third photoacoustic signal.

In one example, the marker is a light-absorbing marker arranged on the surface of the acoustic lens of the probe in the photoacoustic imaging system, for example, on the surface of a side of the acoustic lens facing the target tissue. In another example, the marker may also be a light-absorbing marker added on the acoustic lens, that is, a light-absorbing marker added on the acoustic lens. In yet another example, the marker is a light-absorbing marker on the skin surface corresponding to the target tissue of a test object. In other examples, the marker may also be a light-absorbing marker added in an ultrasonic couplant gel. The ultrasonic couplant gel may usually be a water-based polymer gel coated on the surface of the skin of the test object, or it may be a gel pad that can be directly placed between the probe and the skin to play a coupling role and make the image clearer.

Figure 7:
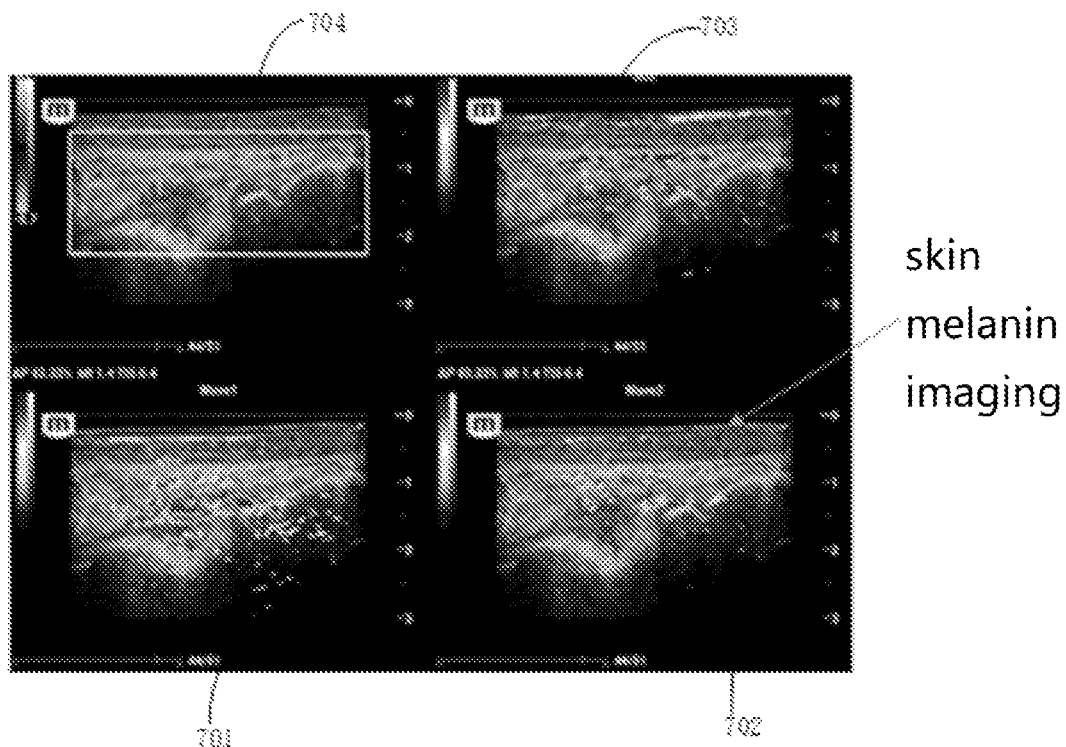
FIG. 7 is a schematic diagram of imaging of melanin in skin surface as the marker in an embodiment of the present application.

The shape of the light-absorbing marker may be any one of the following shapes: lines, dots, polygons, irregular shapes, or any other suitable shapes, such as the lines enclosed in the box in FIG. 7. The size of the lines may be reasonably set according to actual needs, which is not specifically limited here.

The material of the light-absorbing marker may be any material with light-absorbing properties, for example, it may be a dye added with a light-absorbing material, which is not specifically limited here. A light-absorbing mark may be formed on the surface of the acoustic lens by means of spraying, coating or other suitable methods.

During real-time imaging, the imaging content may be continuously updated in real time as the probe moves. It is difficult to have a fixed "standard" that can be used as correction energy in the image. As shown in FIG. 3, since there may be a little light reflected in a coupling medium layer and irradiated to the surface of the acoustic lens, a marker with light absorption (that is, generating a photoacoustic signal) may be drawn on the surface of the lens, and the marker may be a thin line or a point. The light absorption capacity of the marker with respect to the selected wavelength shall be moderate, otherwise it will interfere with the imaging of the detection object. Since part of the light will irradiate the marker, the photoacoustic signal generated may also be received by the ultrasonic probe for imaging.

In another example, the marker is melanin in the skin corresponding to the target tissue of the test object. Since an organism such as human skin may contain melanin which has a strong absorption of light, it can also be used as a reference "standard", as shown in FIG. 7.

However, it is worth mentioning that, in order to avoid the light-absorbing characteristics of the light-absorbing marker being too strong to affect the measurement of blood oxygen, optionally, the first absorption coefficient of the light-absorbing marker with respect to the first optical pulse is lower than the absorption coefficient of the target tissue to the first optical pulse; and the second absorption coefficient of the light-absorbing marker with respect to the second optical pulse is lower than the absorption coefficient of the target tissue to the second optical pulse.

The corresponding photoacoustic signal may be detected by the probe 110. Generally, after the laser 120 generates the first optical pulse, feedback information including an actual transmission time of the first optical pulse may be returned to the processor 105. The processor 105 may calculate the interval time of receiving the photoacoustic signal according to a preset algorithm, and, via the receiving circuit 103, control the probe 110 to receive the first photoacoustic signal from the target tissue and the third photoacoustic signal from the marker.

The first photoacoustic signal and the third photoacoustic signal may be distinguished by the processor 105 based on the interval time of receiving the photoacoustic signals, or they may also be distinguished according to other suitable methods well known to those skilled in the art.

Step S430: controlling the laser to transmit a second optical pulse to the target tissue, wherein the first optical pulse have a first wavelength and the second optical pulse have a second wavelength.

Optionally, the first and second wavelengths may be different; for example, they may be any two different wavelengths in the near-infrared region of 700 nm-900 nm (e.g. the first wavelength $\lambda_1$ is 770 nm and the second wavelength $\lambda_2$ is 830 nm), or any other suitable wavelength range.

As shown in FIG. 3, there is an "optical window" in the near-infrared region of 700 nm-900 nm. In this window, the absorption of water is greatly reduced, the tissue mainly relies on the absorption of oxy-hemoglobin (HbO$_2$) and deoxy-hemoglobin (Hb), and the absorption of light mainly reflects the content of HbO$_2$ and Hb. Therefore, the oxygen content in blood can be inferred at this time by detecting the absorption of light by human tissue.

The first optical pulse and the second optical pulse may be optical pulses transmitted by one laser, which can transmit first optical pulse and second optical pulse in different time periods respectively, and the wavelength of the optical pulses transmitted by this laser can be adjusted. Alternatively, in other examples, the first optical pulse and the second optical pulse may also be transmitted by different lasers.

In addition, there is no limitation in a transmission order of the first optical pulse and the second optical pulse in the embodiments of the present application, and it may be adjusted according to actual application scenarios; for example, the first light may be transmitted first, or the second light may be transmitted first. The specific steps of transmitting the second optical pulse may be similar to the steps of transmitting the first optical pulse in the foregoing step 410, and details thereof are not repeated here.

Step 440: receiving a second acoustic wave generated by the target tissue absorbing the second optical pulse to acquire a second photoacoustic signal, and receiving a fourth acoustic wave generated by the marker absorbing the second optical pulse to acquire a fourth photoacoustic signal. The receiving process of the second photoacoustic signal and the fourth photoacoustic signal may be similar to the receiving process of the first photoacoustic signal and the third photoacoustic signal in the previous step 420, and details thereof are not repeated here.

Step 450: correcting the signal intensity of the first photoacoustic signal based on the signal intensity of the third photoacoustic signal and a first absorption coefficient of the marker with respect to the first optical pulse, and correcting the signal intensity of the second photoacoustic signal based on the fourth photoacoustic signal and a second absorption coefficient of the marker with respect to the second optical pulse.

For example, the first absorption coefficient of the marker with respect to the first optical pulse and the second absorption coefficient of the marker with respect to the second optical pulse can be acquired based on an absorption spectrum (also referred to as an absorption coefficient map) in an imaging wavelength range of the marker. The imaging wavelength range may include the wavelength of the first optical pulse and the wavelength of the second optical pulse.

The signal intensity of the first photoacoustic signal may be corrected; for example, a corrected first photoacoustic signal may be obtained by dividing the signal intensity of the first photoacoustic signal by the signal intensity of the third photoacoustic signal and then multiplying by the first absorption coefficient. With the correction, the calculation result of SaO$_2$ affected by an intensity jump of each frame of photoacoustic images caused by inconsistent laser energy can be rectified. Similarly, the signal intensity of the second photoacoustic signal may be corrected; for example, a corrected second photoacoustic signal may be obtained by divided the signal intensity of the second photoacoustic signal by the signal intensity of the fourth photoacoustic signal and then multiplying by the second absorption coefficient. With the correction, the calculation result of SaO$_2$ affected by an intensity jump of each frame of photoacoustic images caused by inconsistent laser energy can be rectified.

It is worth mentioning that the correction of the first photoacoustic signal in this step may also be performed after step S420 and before step S430.

Step S460: acquiring oxygen saturation of the target tissue based on the corrected signal intensity of the first photoacoustic signal and the corrected signal intensity of the second photoacoustic signal.

Specifically, after the above steps, the calculation formula of the oxygen saturation may be modified as shown in formula (8), so that the oxygen saturation of each pixel may be calculated by the following formula (8):

$$SaO2 = \frac{C_{HbO2}}{C_{Hb} + C_{HbO2}} = \frac{\varepsilon_{Hb}^{\lambda_1} \frac{A^{\lambda_2}}{P^{\lambda_2}} \alpha^{\lambda_2} - \varepsilon_{Hb}^{\lambda_2} \frac{A^{\lambda_1}}{P^{\lambda_1}} \alpha^{\lambda_1}}{\frac{A^{\lambda_1}}{P^{\lambda_1}} \alpha^{\lambda_1} \left(\varepsilon_{HbO2}^{\lambda_2} - \varepsilon_{Hb}^{\lambda_2}\right) + \frac{A^{\lambda_2}}{P^{\lambda_2}} \alpha^{\lambda_2} \left(\varepsilon_{Hb}^{\lambda_1} - \varepsilon_{HbO2}^{\lambda_1}\right)} \times 100\%  \quad (8)$$

where $P^{\lambda_2}$ may represent the intensity of the fourth photoacoustic signal, $P^{\lambda_1}$ may represent the intensity of the third photoacoustic signal, $\alpha^{\lambda_2}$ may represent the second absorption coefficient of the marker with respect to the second optical pulse, $\lambda^{\lambda_1}$ may represent the first absorption coefficient of the marker with respect to the first optical pulse, $A^{\lambda_1}$ may represent signal intensity information of the first photoacoustic signal acquired under the wavelength $\lambda_1$, and $A^{\lambda_2}$ may represent signal intensity information of the second photoacoustic signal acquired under the wavelength $\lambda_2$. The signal intensity information of the first photoacoustic signal may be an amplitude of a corresponding pixel in the first photoacoustic signal, or an amplitude of any one of multiple channels received by the ultrasonic array probe, or a value after beamforming of the amplitude received in each of the multiple channels, etc.; and the signal intensity information of the second photoacoustic signal may be the amplitude of corresponding pixels in the second photoacoustic signal, or the amplitude of any one of multiple channels received by the ultrasonic array probe, or the value after beamforming of the amplitude received in each of the multiple channels, etc.

The meanings represented by other items in formula (8) may refer to the relevant formulas (1) to (7) in the foregoing, which will not be repeated here.

The oxygen saturation of each pixel of the target tissue can be calculated with the above formulas, then the value of the oxygen saturation of each pixel is taken as the pixel value of the corresponding pixel, or the value of the oxygen saturation of each pixel is calculated in accordance with a preset algorithm to obtain the pixel value of the corresponding pixel, and an oxygen saturation image of the target tissue can be obtained based on the pixel value of each pixel.

Further, the method of the embodiment of the present application may also include: acquiring a first photoacoustic image based on the first photoacoustic signal and the third photoacoustic signal, and acquiring a second photoacoustic image based on the second photoacoustic signal and the fourth photoacoustic signal; wherein the first photoacoustic image and the second photoacoustic image may have a marker region corresponding to the marker.

After acquiring the first photoacoustic signal and the third photoacoustic signal, the first photoacoustic signal and the third photoacoustic signal may be denoised and then processed by beamforming and image reconstruction, resulting in obtaining the first photoacoustic image of the target tissue. And, after acquiring the second photoacoustic signal and the fourth photoacoustic signal, the second photoacoustic signal and the fourth photoacoustic signal may be denoised and processed by beamforming and image reconstruction, resulting in obtaining the second photoacoustic image of the target tissue.

In addition, blood vessel-related parameters related to the target tissue, such as the position, shape, oxygen saturation and the like of the target tissue may also be obtained based on the first photoacoustic image and the second photoacoustic image, and the blood oxygen image (i.e. the oxygen saturation image) of the target tissue may be generated according to the blood vessel-related parameters.

In an example, the method of the present application may further comprise: displaying at least one of the following images: the first photoacoustic image, the second photoacoustic image, and the oxygen saturation image.

In one example, the method of the present application may further include: controlling the ultrasonic probe to transmit ultrasonic waves to the target tissue via the transmitting circuit and receive ultrasonic echoes reflected from the target tissue, and acquiring an ultrasound image of the target tissue based on the ultrasonic echoes, wherein the ultrasound image may be one or more of the following mode images: B-mode images, A-mode images, M-mode ultrasound images, contrast-enhanced ultrasound images, and the like.

Optionally, the method of the present application may also display an ultrasound image. For example, as shown in FIG. 7, the ultrasound image 704, the first photoacoustic image 701, the second photoacoustic image 702 and the oxygen saturation image 703 may be displayed simultaneously on the same display interface of the display; accordingly, users can observe the four images at the same time so as to conduct more comprehensive observation and judgment on the condition of the target tissue of the test object.

It is worth mentioning that, the sequence of steps in the method of the present application can be alternately performed or exchanged. In other examples, the present application is implemented by performing measuring and imaging on the oxygen saturation based on two light pulses of different wavelengths. In other examples, it may also be implemented by measuring and imaging oxygen saturation based on more than two light pulses of different wavelengths.

With the methods disclosed in the present application, the signal intensity of the first photoacoustic signal and the signal intensity of the second photoacoustic signal are corrected, thereby calibrating inconsistent laser emission energy and improving the accuracy of the blood oxygen saturation. Moreover, compared with the method using the energy meter, the method of the application is less expensive to implement, and also avoids various problems caused by malfunctioning or inaccurate energy meters, thus enhancing the reliability.

Figure 5:
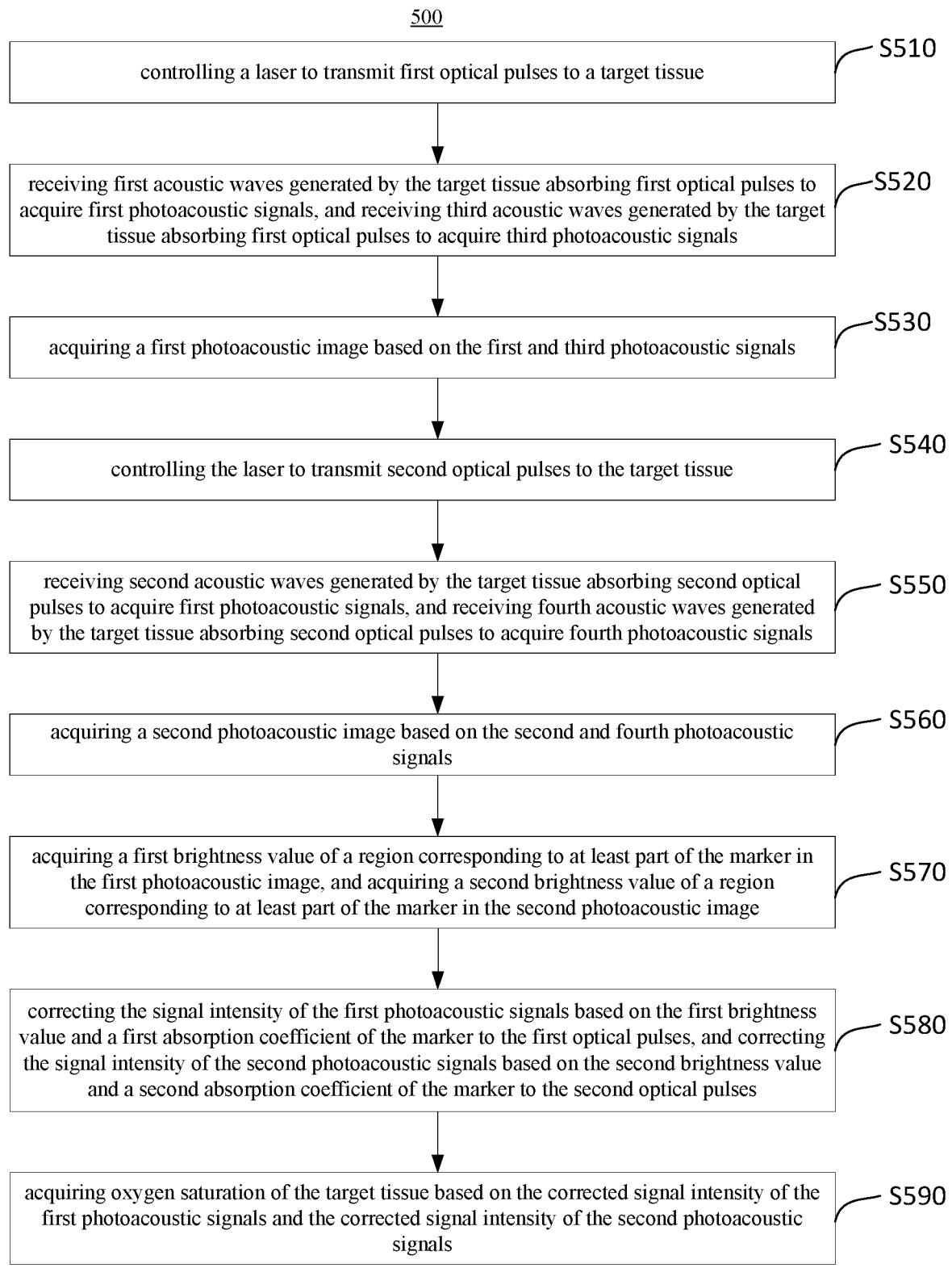
FIG. 5 is a flowchart of a laser energy correction method in a photoacoustic imaging system in another embodiment of the present application.
Figure 6:
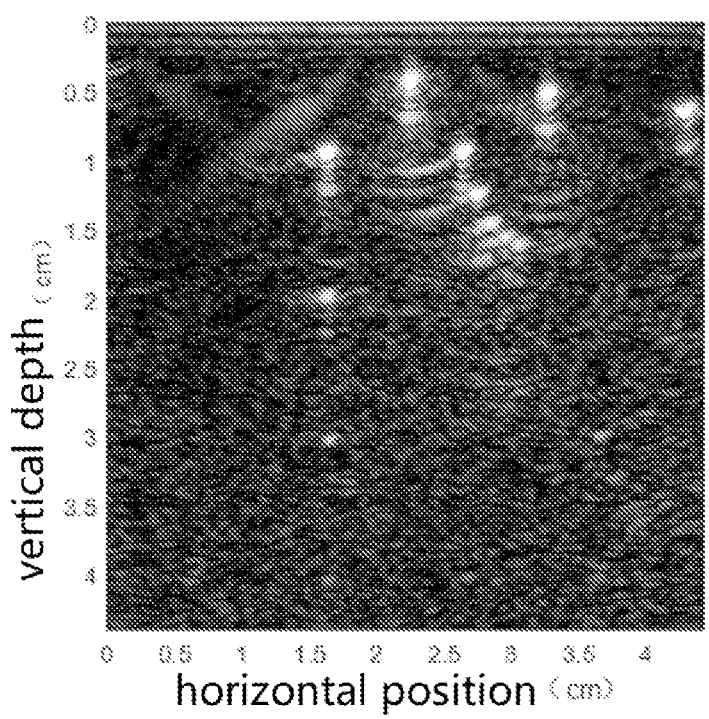
FIG. 6 is a schematic diagram of an image of a marker on a surface of a probe in one embodiment of the present application.

Further, a laser energy correction method in a photoacoustic imaging system may also be provided in the present application, as shown in FIG. 5, the method 500 may include the following steps S510 to S590:

step S510: controlling a laser to transmit first optical pulse to a target tissue;

step S520: receiving a first acoustic wave generated by the target tissue absorbing the first optical pulse to acquire a first photoacoustic signal, and receiving a third acoustic wave generated by a marker absorbing the first optical pulse to acquire a third photoacoustic signal;

step S530: acquiring a first photoacoustic image based on the first photoacoustic signal and the third photoacoustic signal;

step S540: controlling the laser to transmit a second optical pulse to the target tissue;

step S550: receiving a second acoustic wave generated by the target tissue absorbing the second optical pulse to acquire a second photoacoustic signal and receiving a fourth acoustic wave generated by the marker absorbing the second optical pulse to acquire fourth photoacoustic signal;

step S560: acquiring a second photoacoustic image based on the second photoacoustic signal and the fourth photoacoustic signal;

step S570: acquiring a first brightness value of a region corresponding to at least part of the marker in the first photoacoustic image, and acquiring a second brightness value of the region corresponding to at least part of the marker in the second photoacoustic image;

step S580: correcting the signal intensity of the first photoacoustic signal based on the first brightness value and a first absorption coefficient of the marker with respect to the first optical pulse, and correcting the signal intensity of the second photoacoustic signal based on the second brightness value and a second absorption coefficient of the marker with respect to the second optical pulse; and step S590: acquiring the oxygen saturation of the target tissue based on the corrected signal intensity of the first photoacoustic signal and the corrected signal intensity of the second photoacoustic signal.

With the laser energy correction method disclosed in the second aspect of the present application, by acquiring a brightness value of the marker in the photoacoustic image to use the brightness value to correct a corresponding photoacoustic signal, and by acquiring the oxygen saturation of the target tissue based on the corrected first photoacoustic signal and the corrected second photoacoustic signal, inaccurate calculation of blood oxygen saturation caused by inconsistent laser energy can be calibrated, thereby improving the accuracy of oxygen saturation, lowering cost in the method according to the present application than the method of adding hardware.

For the description of steps S510 and S520, reference may be made to the foregoing steps S410 and S420, which will not be repeated here.

In step S530, after the first photoacoustic signal and the third photoacoustic signal are acquired, the first photoacoustic signal and the third photoacoustic signal may be denoised and then processed by beamforming and image reconstruction to obtain the first photoacoustic image of the target tissue.

For the description of steps S540 and S550, reference may be made to the foregoing steps S430 and S440, which will not be repeated here.

In an example, in step S560, after the second photoacoustic signal and the fourth photoacoustic signal are acquired, the second photoacoustic signal and the fourth photoacoustic signal may be denoised and then processed by beamforming and image reconstruction to obtain the second photoacoustic image of the target tissue.

In step S570, the first brightness value of the region corresponding to at least part of the marker in the first photoacoustic image may be obtained, and the second brightness value of the region corresponding to at least part of the marker in the second photoacoustic image may be obtained. The region corresponding to the marker may be first identified from the first photoacoustic image and the second photoacoustic image by any suitable method well known to those skilled in the art, such as a method based on machine learning; in this connection, a database needs to be constructed first. The database of the first photoacoustic image may contain multiple calibration results for the region corresponding to the marker. The method of machine learning may be specifically an end-to-end semantic segmentation network method based on deep learning, which may constructing the network by stacking a base-level convolutional layer and a fully-connected layer, removing the last fully-connected layer of the network, and adding an upsampling or deconvolution layer to make the sizes of the input and output to be the same, so that the region of interest of the input data and its corresponding category can be directly obtained. Common networks may include FCN, U-Net, Mask R-CNN, etc., and the trained network model can be obtained by the above training. Based on the trained network model, the region corresponding to the marker may be divided from the first photoacoustic image and the second photoacoustic image respectively. The first photoacoustic image and the second photoacoustic image may be identified based on different trained network models, or may also be identified based on the same trained network model. For different types of markers, they may also correspond to different trained network models.

In real-time imaging, for each frame of the first photoacoustic image and each frame of the second photoacoustic image, the region of the marker distributed in the images can be segmented and identified.

In an example, acquiring the first brightness value corresponding to at least part of the marker in the first photoacoustic image may include: acquiring pixel values of multiple pixels in at least part of the markers in the first photoacoustic image; and determining the first brightness value based on the pixel values of multiple pixels; wherein the first brightness value may include one of the mean value of the pixel values of multiple pixels, the median value of the pixel values of multiple pixels, or the pixel value corresponding to the peak value of the histogram of the pixel values of multiple pixels.

It is worth mentioning that, in the present application, the region corresponding to at least part of the marker may be a part of the region corresponding to the marker, or may be multiple spaced points in the region corresponding to the marker, or the region corresponding to the entire marker.

In another example, acquiring the second brightness value of at least part of the marker in the second photoacoustic image may include: acquiring the pixel values of multiple pixels in at least part of the marker in the second photoacoustic image; and determining the second brightness value based on the pixel values of multiple pixels; wherein the second brightness value may include the average value of the pixel values of multiple pixels, the median value of the pixel values of multiple pixels, or the pixel value corresponding to the peak value of the histogram of the pixel values of multiple pixels.

Since the brightness of the marker in the photoacoustic image is linearly related to the energy of the laser pulses, the energy of the laser pulses can be corrected by the brightness of the marker in the image, so that the accuracy of the oxygen saturation calculated based on the corrected signal intensities of the first and second photoacoustic signals can be higher. Moreover, compared with the method using the energy meter, the method of the application costs less, and also avoids various problems caused by malfunctioning or inaccurate energy meters, thus enhancing the reliability.

In step S580, correcting the signal intensity of the first photoacoustic signal based on the first brightness value and the first absorption coefficient of the marker with respect to the first optical pulse may, for example, include: dividing the first photoacoustic signal by the first brightness value and then multiplying by the first absorption coefficient so as to obtain the corrected signal intensity of the first photoacoustic signal. For another example, correcting the signal intensity of the second photoacoustic signal based on the second brightness value and the second absorption coefficient of the marker with respect to the second optical pulse may include:
dividing the signal intensity of the second photoacoustic signal by the second brightness value and then multiplying by the second absorption coefficient so as to obtain the corrected signal intensity of the second photoacoustic signal.

In step S590, the oxygen saturation of the target tissue can be acquired based on the corrected signal intensity of the first photoacoustic signal and the corrected signal intensity of the second photoacoustic signal.

Specifically, based on the foregoing steps, the calculation formula of the oxygen saturation may be modified as shown in formula (9) to calculate the oxygen saturation of each pixel point by the following formula (9):

$$SaO2 = \frac{C_{HbO2}}{C_{Hb} + C_{HbO2}} = \frac{\varepsilon_{Hb}^{\lambda_1} \frac{A^{\lambda_2}}{B^{\lambda_2}} \alpha^{\lambda_2} - \varepsilon_{Hb}^{\lambda_2} \frac{A^{\lambda_1}}{B^{\lambda_1}} \alpha^{\lambda_1}}{\frac{A^{\lambda_1}}{B^{\lambda_1}} \alpha^{\lambda_1} \left(\varepsilon_{HbO2}^{\lambda_2} - \varepsilon_{Hb}^{\lambda_2}\right) + \frac{A^{\lambda_2}}{B^{\lambda_2}} \alpha^{\lambda_2} \left(\varepsilon_{Hb}^{\lambda_1} - \varepsilon_{HbO2}^{\lambda_1}\right)} \times 100\% \quad (9)$$

where $B^{\lambda_2}$ represents the second brightness of the region corresponding to the marker in the second photoacoustic image, $B^{\lambda_1}$ represents the first brightness of the region corresponding to the marker in the first photoacoustic image, $\alpha^{\lambda_2}$ represents the second absorption coefficient of the marker with respect to the second optical pulse, $\alpha^{\lambda_1}$ represents the first absorption coefficient of the marker with respect to the first optical pulse, $A^{\lambda_1}$ represents signal intensity information of the first photoacoustic signal acquired under the wavelength $\lambda_1$, and $A^{\lambda_2}$ represents signal intensity information of the second photoacoustic signal acquired under the wavelength $\lambda_2$. The signal intensity information of the first photoacoustic signal may be the amplitude of corresponding pixels in the first photoacoustic signal, or the amplitude of any one of multiple channels received by the ultrasonic array probe, or the value after beamforming of the amplitude received in each of the multiple channels, etc.; and the signal intensity information of the second photoacoustic signal may be the amplitude of corresponding pixels in the second photoacoustic signal, or the amplitude of any one of multiple channels received by the ultrasonic array probe, or the value after beamforming of the amplitude received in each of the multiple channels, etc. . . .

The meanings represented by other items in formula (9) may refer to the relevant formulas (1) to (7) in the foregoing, which will not be repeated here.

The oxygen saturation of each pixel of the target tissue can be calculated with the above formulas, then the value of the oxygen saturation of each pixel may be taken as the pixel value of the corresponding pixel; or the value of the oxygen saturation of each pixel may be calculated in accordance with a preset algorithm to obtain the pixel value of the corresponding pixel, and image of the oxygen saturation of the target tissue can be obtained based on the pixel value of each pixel.

In addition, blood vessel-related parameters related to the target tissue, such as the position, shape, oxygen saturation and the like of the target tissue may also be obtained based on the first photoacoustic image and the second photoacoustic image, and the blood oxygen image (i.e. the oxygen saturation image) of the target tissue may be generated according to the blood vessel-related parameters.

In an example, the method of the present application may further comprise: displaying at least one of the following images: the first photoacoustic image, the second photoacoustic image, and the blood oxygen saturation image.

In one example, the method of the present application may further include: controlling the ultrasonic probe to transmit ultrasonic waves to the target tissue via the transmitting circuit and receive ultrasonic echoes reflected from the target tissue, and acquiring an ultrasound image of the target tissue based on the ultrasonic echoes, wherein the ultrasound image may be one or more of the following mode images: B-mode images, A-mode images, M-mode ultrasound images, contrast-enhanced ultrasound images, and the like.

Optionally, the method of the present application may also display an ultrasound image. For example, as shown in FIG. 7, the ultrasound image (the image in the upper left corner of FIG. 7), the first photoacoustic image (the image in the lower left corner of FIG. 7), the second photoacoustic image (the image in the upper right corner of FIG. 7) and the oxygen saturation image (the image in the lower right corner of FIG. 7) may be displayed simultaneously on the same display interface of the display, so that users can observe the four images at the same time to conduct more comprehensive observation and judgment on the condition of the target tissue of the test object.

It is worth mentioning that, the sequence of steps in the method of the present application can be alternately performed or exchanged. In other examples, the present application is implemented by performing measuring and imaging on the oxygen saturation based on two light pulses of different wavelengths. In other examples, it may also be implemented by measuring and imaging oxygen saturation based on more than two light pulses of different wavelengths.

With the laser energy correction method disclosed in the embodiments of the present application, by acquiring a brightness value of the marker in the photoacoustic image to use the brightness value to correct a corresponding photoacoustic signal, and by acquiring the oxygen saturation of the target tissue based on the corrected first photoacoustic signal and the corrected second photoacoustic signal, the accuracy of oxygen saturation can be improved, and the method according to the present application is less costly than the method of adding hardware.

Figure 8:
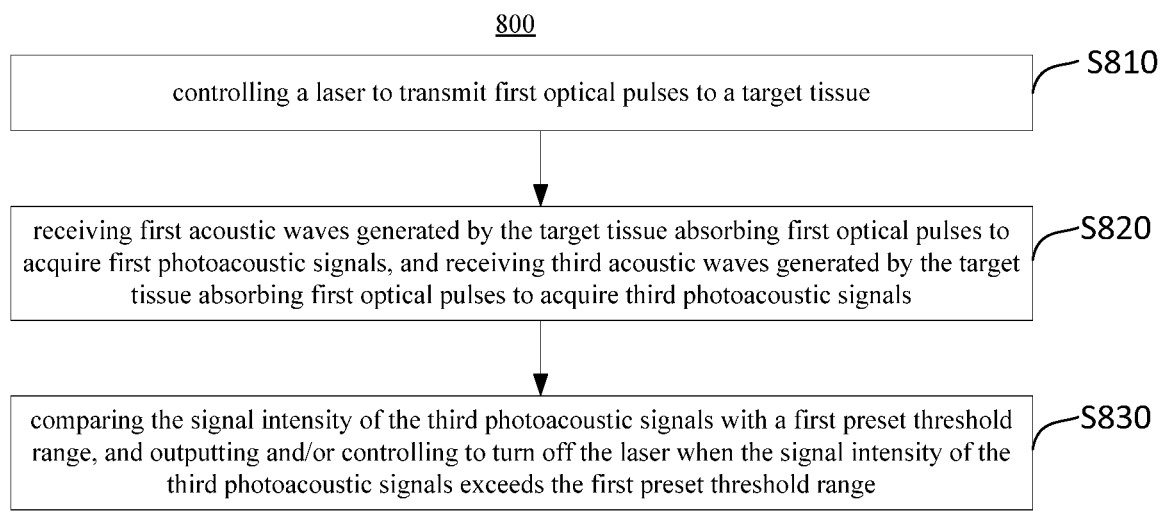
FIG. 8 is a flowchart of a laser energy prompting method in a photoacoustic imaging system in an embodiment of the present application.

Further, a laser energy prompting method in a photoacoustic imaging system may also be provided in the present application, as shown in FIG. 8, the method 800 may include the following steps S810 to S830:

step S810: controlling a laser to transmit a first optical pulse to a target tissue;

step S820: receiving a first acoustic wave generated by the target tissue absorbing the first optical pulse to acquire a first photoacoustic signal and receiving a third acoustic wave generated by the marker absorbing the first optical pulse to acquire a third photoacoustic signal; and step S830: comparing the signal intensity of the third photoacoustic signal with a first preset threshold range, and outputting prompt information and/or controlling to turn off the laser when the signal intensity of the third photoacoustic signal exceeds the first preset threshold range.

Since the signal intensity of the third photoacoustic signal is positively correlated with the laser pulse energy, the signal intensity of the third photoacoustic signal can be compared with the first preset threshold range, and when the signal intensity of the third photoacoustic signal exceeds the first preset threshold range, it indicates that the laser pulse energy might exceed a safety upper limit, a prompt message may thus be outputted to prompt users that the laser pulse energy exceeds the safety range, so that the laser may be turned off by users in time and the laser pulse energy for subsequent detection may be lowered, thereby avoiding damage to the test object's tissue after the laser pulse energy exceeds the safety specification; or, it may be also possible to directly control the shutdown of the laser to avoid damage to the tissue of the test object due to excessive laser pulse energy; or, it may also output prompt information while controlling the laser to turn off, thereby avoiding damage to the test object's tissue caused by excessive laser pulse energy, and prompting users to lower the laser pulse energy for subsequent detection.

For the relevant details of each step in this embodiment, reference may also be made to the foregoing related descriptions. For example, for the relevant details of steps S810 and S820, reference may be made to the foregoing steps S410 and S420, etc.

In step S830, the first preset threshold range may be determined according to a safety upper limit value of the. For example, the first preset threshold value range may be obtained by measurement in advance. In this example, if the safety upper limit value of the laser pulse is set as Emax, the signal intensity of the photoacoustic signal generated by the absorption of the marker with respect to the first optical pulse having the optical pulse energy of Emax can be obtained when the optical pulse energy is Emax, so that the signal intensity of the photoacoustic signal may be taken as the first preset threshold range. It is worth mentioning that the first preset threshold range may be a fixed signal intensity of a photoacoustic signal, or may be a range value of a signal intensity of a photoacoustic signal.

During real-time imaging, the signal intensity of third photoacoustic signal is compared with the first preset threshold range; and when the signal intensity of the third photoacoustic signal exceeds the first preset threshold range, it indicates that the laser pulse energy is likely to exceed the safety upper limit, in this connection, it may output prompt information and/or control to turn off the laser, thereby avoiding damage to the target tissue of the test object due to the laser pulse energy exceeding the safety upper limit.

Optionally, the way to output the prompt information may include, for example, displaying the prompt information on the display interface of the display of the photoacoustic imaging system, or prompting by audible and/or light flashing alarm via an audible and visual alarm device, or prompting by voice broadcast via a loudspeaker or the like. Alternatively, more than one of the above prompt manners may be used to prompt.

In an example, the method of the present application may further include the following steps S840 to S860 (not shown in the figure):

step S840: controlling the laser to transmit a second optical pulse to the target tissue, the first optical pulse having a first wavelength and the second optical pulse having a second wavelength;

step S850: receiving a second acoustic wave generated by the target tissue absorbing second optical beams to acquire a second photoacoustic signal and receiving a fourth acoustic wave generated by the marker absorbing the second optical pulse to acquire a fourth photoacoustic signal; and step S860: comparing the signal intensity of the fourth photoacoustic signal with a second preset threshold range, and outputting prompt information and/or controlling to turn off the laser when the signal intensity of the fourth photoacoustic signal exceeds the second preset threshold range.

Similarly, for the relevant details of steps S840 to S850, reference may be made to the foregoing related descriptions, such as the steps S430 and S440. In step S860, the acquisition of the second preset threshold range is similar to that of the first preset threshold range; that is, the second preset threshold value range can be obtained by measurement in advance. For example, if the safety upper limit value of the laser pulse is set as Emax, the signal intensity of the photoacoustic signal generated by the marker absorbing the second optical pulse having the optical pulse energy of Emax can be obtained when the optical pulse energy is Emax, so that the signal intensity of the photoacoustic signal may be taken as the second preset threshold range. It is worth mentioning that the second preset threshold range may be a fixed signal intensity of a photoacoustic signal, or may be a range value of a signal intensity of a photoacoustic signal. It is worth mentioning that since the absorption coefficients of the marker with respect to the first and second optical pulses may be different, the sizes of the first preset threshold range and the second preset threshold range may also be different, or they may be the same when the absorption coefficients are not different.

During real-time imaging, the signal intensity of fourth photoacoustic signal is compared with the second preset threshold range; and when the signal intensity of the fourth photoacoustic signal exceeds the second preset threshold range, it may indicate that the laser pulse energy might be likely to exceed the safety upper limit, in this connection, it may output prompt information and/or control to turn off the laser, thereby avoiding damage to the target tissue of the test object due to the laser pulse energy exceeding the safety upper limit.

Optionally, the way to output the prompt information may include, for example, displaying the prompt information on the display interface of the display of the photoacoustic imaging system, or prompting by audible and/or light flashing alarm via an audible and visual alarm device, or prompting by voice broadcast via a loudspeaker or the like. Alternatively, more than one of the above prompt manners may be used to prompt.

During the above real-time imaging process, the laser energy may be continuously monitored.

In an example, the method of the present application may further comprise: when transmitting the first optical pulse, the emission intensity of the laser is controlled based on the signal intensity of the third photoacoustic signal. For example, when the emission intensity of the laser exceeds the aforesaid first preset threshold range, the emission intensity of the laser is controlled to be lowered so that the optical pulse energy transmitted by the laser is lower than the safety upper limit; or, when the signal intensity of the third photoacoustic signal is lower than the first preset threshold, the emission intensity of the laser is controlled to be heightened to further improve imaging quality. The first preset threshold may be a preset value, which is not specifically limited herein.

Alternatively, according to the signal intensity of the third photoacoustic signal, it may be also possible to output an adjustment suggestion for the emission intensity of the laser, etc.; or according to the signal intensity of the fourth photoacoustic signal, an adjustment suggestion for the transmission of the laser may be outputted, so that the emission intensity of the laser can be adjusted by users according to the adjustment suggestion, such as turning up or down the emission strength, according to the adjustment suggestions.

In an example, the method of the present application may further comprise: when transmitting the second optical pulse, the emission intensity of the laser may be controlled based on the signal intensity of the fourth photoacoustic signal. For example, when the emission intensity of the laser exceeds the aforesaid second preset threshold range, the emission intensity of the laser may be controlled to be lower so that the optical pulse energy transmitted by the laser is lower than the safety upper limit; alternatively, when the signal intensity of the fourth photoacoustic signal is lower than the second preset threshold, it may be also possible to control to increase the emission intensity of the laser to further improve the imaging quality. The second preset threshold may be a preset value, which is not specifically limited here.

In an example, the method of the preset disclosure may further comprise: when transmitting the first optical pulse, determining a process manner of the first photoacoustic signal based on the signal intensity of the third photoacoustic signal. For example, when the signal intensity of the third photoacoustic signal is lower than the first preset intensity, the process manner may be to perform gain compensation on the first photoacoustic signal. The first preset intensity may be a value preset according to prior experience, which is not specifically limited herein.

In another example, the method of the preset disclosure may further comprise: when transmitting the second optical pulse, determining a process manner of the second photoacoustic signal based on the signal intensity of the fourth photoacoustic signal. For example, when the signal intensity of the fourth photoacoustic signal is lower than the second preset intensity, the process manner of the second photoacoustic signal may be to perform gain compensation on the second photoacoustic signal. The second preset intensity may be a value preset according to prior experience, which is not specifically limited herein.

In an embodiment of the present application, it may also be possible to acquire a first photoacoustic image based on the first photoacoustic signal and the third photoacoustic signal, acquire a second photoacoustic image based on the second photoacoustic signal and the fourth photoacoustic signal, and calculate the oxygen saturation of each pixel to further draw an oxygen saturation image. The specific process may refer to the previous description, which will not be repeated here.

It is worth mentioning that, the sequence of steps in the method of the present application can be alternately performed or exchanged. In other examples, the present application is implemented by performing measuring and imaging on the oxygen saturation based on two light pulses of different wavelengths. In other examples, it may also be implemented by measuring and imaging oxygen saturation based on more than two light pulses of different wavelengths.

With the laser energy prompting method disclosed in the embodiments of the present application, by comparing the third photoacoustic signal with the first preset threshold range, and outputting prompt information and/or controlling to turn off the laser source when the signal intensity of the third photoacoustic signal exceeds the first preset threshold range, damage to the target tissue caused by the energy of the first optical pulse transmitted by the light source exceeding a safety range can be avoided, thereby improving the safety and reliability of the photoacoustic imaging system.

Figure 9:
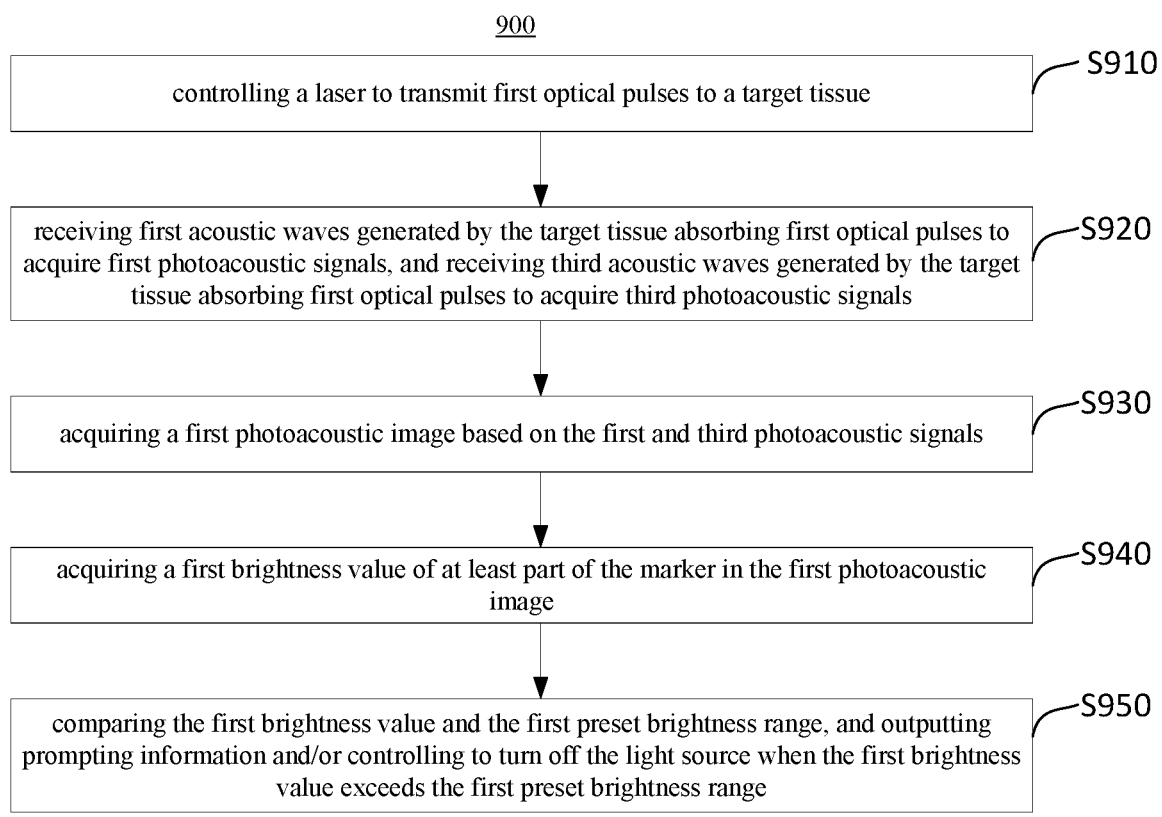
FIG. 9 is a flowchart of a laser energy prompting method in a photoacoustic imaging system in another embodiment of the present application.

Further, the laser pulse energy may also be measured by the brightness of the region corresponding to the marker in the photoacoustic image to realize monitoring the laser pulse energy, which is a real-time monitoring during the imaging process. As shown in FIG. 9, a laser energy prompting method 900 in a photoacoustic imaging system further provided in the present application may include the following steps S910 to S950:

step S910: controlling a laser to transmit a first optical pulse to a target tissue;

step S920: receiving a first acoustic wave generated by the target tissue absorbing the first optical pulse to acquire a first photoacoustic signal, and receiving a third acoustic wave generated by the marker absorbing the first optical pulse to acquire a third photoacoustic signal;

step S930: acquiring a first photoacoustic image based on the first photoacoustic signal and the third photoacoustic signal;

step S940: acquiring a first brightness value of at least part of the marker in the first photoacoustic image; and step S950: comparing the first brightness value and a first preset brightness range, and outputting prompt information and/or controlling to turn off the light source when the first brightness value exceeds the first preset brightness range.

With the laser energy prompting method disclosed in the present application, by acquiring the first brightness value of at least part of the marker in the first photoacoustic image, comparing the first brightness value with the first preset brightness range, and outputting prompting information and/or controlling to turn off the laser when the first brightness value exceeds the first preset brightness range, damage to the target tissue caused by the energy of the first optical pulse transmitted by the laser exceeding a safety range can be avoided, thereby improving the safety and reliability of the photoacoustic imaging system.

For the relevant details of steps S910 to S950 in this embodiment, reference may also be made to the foregoing related descriptions. For example, for the relevant details of step S940, reference may be made to the foregoing steps S570.

The difference in this embodiment from the previous embodiments may include that in this embodiment, the intensity of the laser pulse energy is measured by the brightness value of the marker, so that when the safety upper limit is exceeded, a prompt message is outputted and/or the light source is controlled to be turned off.

In step S950, when the first brightness value exceeds the first preset threshold range, it may indicate that the laser pulse energy may exceed the safety upper limit, the prompt message may thus be outputted to prompt users that the laser pulse energy exceeds the safety range, so that the laser can be turned off in time and lower the laser pulse energy for subsequent detection, thereby avoiding damage to the test object's tissue after the laser pulse energy exceeds the safety specification; or, it is also possible to directly control the shutdown of the laser to avoid damage to the tissue of the test object due to excessive laser pulse energy; or, it can also output prompt information while controlling the laser to turn off, thereby avoiding damage to the test object's tissues caused by excessive laser pulse energy, and prompting the user to lower the laser pulse energy for subsequent detection.

In step S950, the first preset brightness range may be obtained by measurement in advance. For example, if the safety upper limit value of the laser pulse is set to Emax, the photoacoustic signal generated by the marker absorbing the first optical pulse having the optical pulse energy of Emax can be obtained under the condition that the optical pulse energy is Emax, and the photoacoustic image of the marker is generated based on the photoacoustic signals. The average brightness Pmax of the pixels in the photoacoustic image of the marker is obtained, so that the average brightness Pmax is used as the first preset brightness range. It is worth mentioning that the first preset brightness range may be a fixed value or a range value. The average brightness Pmax can also be replaced by, for example, the median value, the peak value of the histogram, or the brightness value of any pixel in the photoacoustic image of the marker.

During real-time imaging, the first brightness may be compared with the first preset threshold range; and when the first brightness exceeds the first preset threshold range, it may indicate that the laser pulse energy might be likely to exceed the safety upper limit, in this connection, a prompt message may be outputted and/or the laser may be turned off, thereby avoiding damage to the target tissue of the test object due to the laser pulse energy exceeding the safety upper limit.

Optionally, the way to output the prompt information may include, for example, displaying the prompt information on the display interface of the display of the photoacoustic imaging system, or prompting by audible and/or light flashing alarm via an audible and visual alarm device, or prompting by voice broadcast via a loudspeaker or the like. Alternatively, more than one of the above prompt manners may be used to prompt.

In an example, the method of the present application may further comprise the following steps S960 to S9100 (not shown in the figure):
  step S960: controlling the laser to transmit a second optical pulse to the target tissue;
  step S970: receiving a second acoustic wave generated by the target tissue absorbing the second optical pulse to acquire a second photoacoustic signal, and receiving a fourth acoustic wave generated by the marker absorbing the second optical pulse to acquire a fourth photoacoustic signal;
  step S980: acquiring a second photoacoustic image based on the second photoacoustic signal and the fourth photoacoustic signal;
  step S990: acquiring a second brightness value of at least part of the marker in the second photoacoustic image; and
  step S9110: comparing the second brightness value with the second preset brightness range, and outputting prompt information and/or controlling to turn off light source when the second brightness value exceeds the second preset brightness range.

Similarly, for the relevant details of steps S960 to S990 in this embodiment, reference may also be made to the foregoing related descriptions.

In step S9100, the acquisition of the second preset threshold range is similar to that of the first preset threshold range; that is, the second preset threshold value range may be obtained by measurement in advance. For example, if the safety upper limit value of the laser pulse is set as Emax, the signal intensity of the photoacoustic signal generated by the marker absorbing the second optical pulse with the optical pulse energy of Emax can be obtained when the optical pulse energy is Emax, the photoacoustic signal generated by the marker absorbing the second optical pulse with the optical pulse energy of Emax can be obtained when the optical pulse energy is Emax, and the photoacoustic image of the marker may be generated based on the photoacoustic signal. The average brightness Pmax of the pixels in the photoacoustic image of the marker may be obtained, so that the average brightness Pmax is used as the second preset brightness range. It is worth mentioning that the second preset brightness range may be a fixed value or a range value. The average brightness Pmax may also be replaced by, for example, the median value, the peak value of the histogram, or the brightness value of any pixel in the photoacoustic image of the marker.

It is worth mentioning that since the absorption coefficients of the marker with respect to the first and second optical pulse may be different, the sizes of the first preset threshold range and the second preset threshold range may also be different, or they may be the same when there is little difference between the absorption coefficients.

During real-time imaging, the second brightness value is compared with the second preset threshold range; and when the second brightness value exceeds the second preset threshold range, it may indicate that the laser pulse energy might be likely to exceed the safety upper limit, in this connection, a prompt message may be outputted and/or the laser may be turned off, thereby avoiding damage to the target tissue of the test object due to the laser pulse energy exceeding the safety upper limit.

Optionally, the way to output the prompt information may include, for example, displaying the prompt information on the display interface of the display of the photoacoustic imaging system, or prompting by audible and/or light flashing alarm via an audible and visual alarm device, or prompting by voice broadcast via a loudspeaker or the like. Alternatively, more than one of the above prompt manners may be used to prompt.

During the above real-time imaging process, the laser energy may be continuously monitored.

In an example, the method of the present application may further comprise: when transmitting the first optical pulse, the emission intensity of the laser may be controlled based on the first brightness value. For example, when the emission intensity of the laser exceeds the aforesaid first preset threshold range, the emission intensity of the laser may be controlled to be lower so that the optical pulse energy transmitted by the laser is lower than the safety upper limit; or, when the first brightness value is lower than the first preset threshold, it may be also possible to control to increase the emission intensity of the laser to further improve the imaging quality. The second preset threshold may be a preset value, which is not specifically limited here.

Alternatively, according to the first brightness value, it may be also possible to output an adjustment suggestion for the emission intensity of the laser, etc.; or according to the second brightness value, an adjustment suggestion for the transmission of the laser may be outputted, so that the laser can be adjusted by users according to the adjustment suggestion, such as reducing or increasing the emission strength, according to the adjustment suggestions.

In an example, the method of the present application may further comprise: when transmitting the second optical pulse, the emission intensity of the laser may be controlled based on the second brightness value. For example, when the emission intensity of the laser exceeds the aforesaid second preset brightness range, the emission intensity of the laser may be controlled to be lower so that the optical pulse energy transmitted by the laser is lower than the safety upper limit; alternatively, when the second brightness value is lower than the second brightness threshold, it is also possible to control to increase the emission intensity of the laser to further improve the imaging quality. The second brightness threshold may be a preset value, which is not specifically limited here.

In an example, the method of the preset disclosure may further comprise: determining the process manner of the second photoacoustic signal based on the first brightness value. For example, when the first brightness value is lower than the first preset brightness, the process manner may be to perform gain compensation on the first photoacoustic signal. The first preset brightness may be a value preset according to prior experience, which is not specifically limited herein.

In another example, the method of the preset disclosure may further comprise: when transmitting the second optical pulse, determining the process manner of the second photoacoustic signal based on the second brightness value. For example, when the second brightness value is lower than the second preset brightness, the process manner of the second photoacoustic signal is to perform gain compensation on the second photoacoustic signal. The second preset intensity may be a value preset according to prior experience, which is not specifically limited herein. The first preset brightness and the second preset brightness may be the same value, or different values.

In an embodiment of the present application, it is possible to acquire the first photoacoustic image based on the first photoacoustic signal and the third photoacoustic signal, acquire the second photoacoustic image based on the second photoacoustic signal and the fourth photoacoustic signal, and calculate the oxygen saturation of each pixel to further draw an image of the oxygen saturation. The specific process can refer to the previous description, which will not be repeated here.

It is worth mentioning that, in various embodiments of the present application, the oxygen saturation image may be displayed, or the oxygen saturation of one or more pixels may be displayed.

It is worth mentioning that, the sequence of steps in the method of the present application can be alternately performed or exchanged. In other examples, the present application is implemented by performing measuring and imaging on the oxygen saturation based on two light pulses of different wavelengths. In other examples, it may also be implemented by measuring and imaging oxygen saturation based on more than two light pulses of different wavelengths.

With the laser energy prompting method disclosed in the embodiments of the present application, by acquiring the first brightness value of at least part of the marker in the first photoacoustic image, comparing the first brightness value with the first preset brightness range, and outputting prompting information and/or controlling to turn off the laser when the first brightness value exceeds the first preset brightness range, damage to the target tissue caused by the energy of the first optical pulse transmitted by the laser exceeding a safety range can be avoided, thereby improving the safety and reliability of the photoacoustic imaging system.

A photoacoustic imaging system configured to implement the above method 400, 500, 800, or 900 is also provided in the present application. The system may include: an ultrasonic probe 110, a laser 120, a receiving circuit 103, a memory 107, a processor 105, a display 106 and so on. Referring to FIG. 1 again, the photoacoustic imaging system may be realized as the photoacoustic imaging system 100 as shown in FIG. 1, in this connection, the ultrasonic imaging system 100 may include the ultrasonic probe 110, the laser 120, the receiving circuit 103, the memory 107, the processor 105, the display 106 and so on. Optionally, the photoacoustic imaging system 100 may further include the transmitting/receiving selection switch 102, the mechanical scanner 130 and the like. The laser 120 may be configured to transmit the first optical pulse and the second optical pulse to the target tissue, the first optical pulse having a first wavelength and the second optical pulse having a second wavelength; the receiving circuit 103 may be configured to control the ultrasonic probe 110 to receive first acoustic wave generated by the target tissue absorbing the first optical pulse to acquire the first photoacoustic signal, control the ultrasonic probe 110 to receive the second acoustic wave generated by the target tissue absorbing the second optical pulse to acquire the second photoacoustic signal, control the ultrasonic probe 110 to receive the third acoustic wave generated by the marker absorbing the first optical pulse to acquire the third photoacoustic signal, and receive the fourth acoustic wave generated by the marker absorbing the second optical pulse to acquire the fourth photoacoustic signal.

The memory 107 may be configured to store executable program instructions; and the processor 106 may be also configured to execute the program instructions stored in the memory, so that the processor executes the aforementioned method 400, 500, 800, or 900.

The display 106 may be configured for displaying visual information, for example, displaying at least one of the following information: the photoacoustic image, the ultrasound image, the blood oxygen saturation image, the prompt information, and the like.

In addition, in one example, the marker such as a light-absorbing marker may be arranged on the surface of the acoustic lens of the probe of the photoacoustic imaging system for the acoustic lens of the ultrasound probe, or the marker such as a light-absorbing marker may also be added on the acoustic lens. For specific details, reference may also be made to the foregoing related descriptions, which will not be repeated here.

Since the photoacoustic imaging system of the present application can realize the aforementioned method, it also has the advantages of the aforementioned method.

In addition, an embodiment of the present invention further provides a computer storage medium, on which a computer program is stored. One or more computer program instructions may be stored on a computer-readable storage medium, the processor may execute program instructions stored in the storage device to implement the functions (implemented by the processor) in the embodiments of the present invention herein and/or other desired functions (e.g., to perform the laser energy correction method according to the embodiments of the present invention and corresponding steps of the laser energy prompting method), and various application programs and various data (such as various data used and/or generated by the application program, etc.) may also be stored in the computer-readable storage medium.

For example, the computer storage medium may include a memory card of a smart phone, a storage component of a tablet computer, a hard disk of a personal computer, a read-only memory (ROM), an erasable programmable read-only memory (EPROM), a portable compact disk read-only memory (CD-ROM), a USB memory, or any combination of the above storage media.

While exemplary embodiments have been described herein with reference to the accompanying drawings, it should be understood that the above example embodiments are merely illustrative and are not intended to limit the scope of the disclosure thereto. Those skilled in the art may make various changes and modifications therein without departing from the scope and spirit of the disclosure. All such changes and modifications are intended to be included in the scope of the disclosure as claimed in the appended claims.

A person of ordinary skill in the art may be aware that, in combination with the examples described in the embodiments disclosed in this specification, units and algorithm steps may be implemented by using electronic hardware or a combination of computer software and electronic hardware. Whether the functions are performed by hardware or software depends on particular applications and design constraint conditions of the technical solutions. Those skilled in the art could use different methods to implement the described functions for each particular application, but such implementation should not be considered to be beyond the scope of the disclosure.

In several embodiments provided in the present application, it should be understood that the disclosed devices and methods may be implemented in other ways. For example, the device embodiments described above are merely exemplary. For example, the division of units is merely a logical function division. In actual implementations, there may be other division methods. For example, a plurality of units or components may be combined or integrated into another device, or some features may be omitted or not implemented.

A large number of specific details are explained in this specification provided herein. However, it can be understood that the embodiments of the disclosure can be practiced without these specific details. In some instances, well-known methods, structures, and technologies are not shown in detail, so as not to obscure the understanding of this description.

Similarly, it should be understood that in order to simplify the disclosure and help to understand one or more of various aspects of the disclosure, in the description of the exemplary embodiments of the disclosure, various features of the disclosure are sometimes together grouped into an individual embodiment, figure or description thereof. However, the method of the disclosure should not be construed as reflecting the following intention, namely, the disclosure set forth requires more features than those explicitly stated in each claim. More precisely, as reflected by the corresponding claims, the inventive point thereof lies in that features that are fewer than all the features of an individual embodiment disclosed may be used to solve the corresponding technical problem. Therefore, the claims in accordance with the particular embodiments are thereby explicitly incorporated into the particular embodiments, wherein each claim itself serves as an individual embodiment of the disclosure.

Those skilled in the art should understand that, in addition to the case where features are mutually exclusive, any combination may be used to combine all the features disclosed in this specification (along with the appended claims, abstract, and drawings) and all the processes or units of any of methods or devices as disclosed. Unless explicitly stated otherwise, each feature disclosed in this specification (along with the appended claims, abstract, and drawings) may be replaced by an alternative feature that provides the same, equivalent, or similar object.

Furthermore, those skilled in the art should understand that although some of the embodiments described herein comprise some but not other features included in other embodiments, combinations of features of different embodiments are meant to be within the scope of the disclosure, and form different embodiments. For example, in the claims, any one of the embodiments set forth thereby can be used in any combination.

Various embodiments regarding components in the disclosure may be implemented in hardware, or implemented by software modules running on one or more processors, or implemented in a combination thereof. It should be understood for those skilled in the art that a microprocessor or a digital signal processor (DSP) may be used in practice to implement some or all of the functions of some modules according to the embodiments of the disclosure. The disclosure may further be implemented as an apparatus program (e.g. a computer program and a computer program product) for executing some or all of the methods described herein. Such a program for implementing the disclosure may be stored on a computer-readable medium, or may be in the form of one or more signals. Such a signal may be downloaded from an Internet website, or provided on a carrier signal, or provided in any other form.

It should be noted that the description of the disclosure made in the above-mentioned embodiments is not to limit the disclosure, and those skilled in the art may design alternative embodiments without departing from the scope of the appended claims. In the claims, any reference signs placed between parentheses should not be construed as limitation on the claims. The word "comprising" does not exclude the presence of elements or steps not listed in a claim. The word "a" or "an" preceding an element does not exclude the presence of a plurality of such elements. The disclosure may be implemented by means of hardware comprising several different elements and by means of an appropriately programmed computer. In unit claims listing several ultrasound devices, several of these ultrasound devices may be specifically embodied by one and the same item of hardware. The use of the terms "first", "second", "third", etc. does not indicate any order. These terms may be interpreted as names.

What is claimed is:

1. A laser energy correction method in a photoacoustic imaging system, comprising:
   controlling a laser to transmit a first optical pulse to a target tissue;
   receiving a first acoustic wave generated by the target tissue absorbing the first optical pulse to acquire a first photoacoustic signal, and receiving a third acoustic wave generated by a marker absorbing the first optical pulse to acquire a third photoacoustic signal;
   controlling the laser to transmit a second optical pulse to the target tissue, the first optical pulse having a first wavelength and the second optical pulse having a second wavelength different from the first wavelength;
   receiving a second acoustic wave generated by the target tissue absorbing the second optical pulse to acquire a second photoacoustic signal, and receiving a fourth acoustic wave generated by the marker absorbing the second optical pulse to acquire a fourth photoacoustic signal;
   correcting a signal intensity of the first photoacoustic signal based on a signal intensity of the third photoacoustic signal together with a first absorption coefficient of the marker with respect to the first optical pulse, and correcting a signal intensity of the second photoacoustic signal based on the fourth photoacoustic signal together with a second absorption coefficient of the marker with respect to the second optical pulse; and
   acquiring an oxygen saturation of the target tissue based on the corrected signal intensity of the first photoacoustic signal and the corrected signal intensity of the second photoacoustic signal,
   wherein a material of the marker comprises a material with light-absorbing properties, and the first absorption coefficient of the marker with respect to the first optical pulse and the second absorption coefficient of the marker with respect to the second optical pulse are capable of being acquired based on an absorption spectrum in an imaging wavelength range of the marker.

2. A laser energy correction method in a photoacoustic imaging system, comprising:

controlling a laser to transmit a first optical pulse to a target tissue;
receiving a first acoustic wave generated by the target tissue absorbing the first optical pulse to acquire a first photoacoustic signal, and receiving a third acoustic wave generated by a marker absorbing the first optical pulse to acquire a third photoacoustic signal;
acquiring a first photoacoustic image based on the first photoacoustic signal and the third photoacoustic signal;
controlling the laser to transmit a second optical pulse to the target tissue;
receiving a second acoustic wave generated by the target tissue absorbing the second optical pulse to acquire a second photoacoustic signal, and receiving a fourth acoustic wave generated by the marker absorbing the second optical pulse to acquire a fourth photoacoustic signal;
acquiring a second photoacoustic image based on the second photoacoustic signal and the fourth photoacoustic signal;
acquiring a first brightness value of a region corresponding to at least part of the marker in the first photoacoustic image, and acquiring a second brightness value of the region corresponding to at least part of the marker in the second photoacoustic image;
correcting a signal intensity of the first photoacoustic signal based on the first brightness value together with a first absorption coefficient of the marker with respect to the first optical pulse, and correcting a signal intensity of the second photoacoustic signal based on the second brightness value together with a second absorption coefficient of the marker with respect to the second optical pulse; and
acquiring an oxygen saturation of the target tissue based on the corrected signal intensity of the first photoacoustic signal and the corrected signal intensity of the second photoacoustic signal,
wherein a material of the marker comprises a material with light-absorbing properties, and the first absorption coefficient of the marker with respect to the first optical pulse and the second absorption coefficient of the marker with respect to the second optical pulse are capable of being acquired based on an absorption spectrum in an imaging wavelength range of the marker.

3. The method according to claim 1, wherein the marker is a light-absorbing marker arranged on a surface of an acoustic lens of a probe of the photoacoustic imaging system; or
the marker is melanin in a skin corresponding to the target tissue of a test object; or
the marker is a light-absorbing marker on a surface of a skin corresponding to the target tissue of a test object; or
the marker is a light-absorbing marker added on the acoustic lens; or
the marker is a light-absorbing marker added in an ultrasonic couplant gel.

4. The method according to claim 3, wherein the first absorption coefficient of the light-absorbing marker with respect to the first optical pulse is lower than an absorption coefficient of the target tissue to the first optical pulse; and
the second absorption coefficient of the light-absorbing marker with respect to the second optical pulse is lower than an absorption coefficient of the target tissue to the second optical pulse.

5. The method according to claim 3, wherein a shape of the light-absorbing marker arranged on the surface of the acoustic lens of the probe of the photoacoustic imaging system comprises one of the following shapes: line, point, polygon, and irregular shape.

6. The method according to claim 2, wherein acquiring a first brightness value of a region corresponding to at least part of the marker in the first photoacoustic image comprises:
acquiring pixel values of multiple pixels in the region corresponding to at least part of the marker in the first photoacoustic image; and
determining the first brightness value based on the pixel values of multiple pixels, wherein the first brightness value comprises one of a mean value of the pixel values of multiple pixels, a median value of the pixel values of multiple pixels, and a pixel value corresponding to a peak value of a histogram of the pixel values of multiple pixels.

7. The method according to claim 2, wherein acquiring a second brightness value of the region corresponding to at least part of the marker in the second photoacoustic image comprises:
acquiring pixel values of multiple pixels in the region corresponding to at least part of the marker in the second photoacoustic image; and
determining the second brightness value based on the pixel values of multiple pixels, wherein the second brightness value comprises a mean value of the pixel values of multiple pixels, a median value of the pixel values of multiple pixels, or a pixel value corresponding to a peak value of a histogram of the pixel values of multiple pixels.

8. The method according to claim 2, wherein correcting a signal intensity of the first photoacoustic signal based on the first brightness value together with a first absorption coefficient of the marker with respect to the first optical pulse and correcting a signal intensity of the second photoacoustic signal based on the second brightness value together with a second absorption coefficient of the marker with respect to the second optical pulse comprise:
dividing the signal intensity of the first photoacoustic signal by the first brightness value and then multiplying by the first absorption coefficient to acquire the corrected signal intensity of the first photoacoustic signal; and
dividing the signal intensity of the second photoacoustic signal by the second brightness value and then multiplying by the second absorption coefficient to acquire the corrected signal intensity of the second photoacoustic signal.

9. The method according to claim 2, further comprising:
displaying the first photoacoustic image, the second photoacoustic image and an image of the oxygen saturation.

10. The method according to claim 1, wherein a wavelength of a light transmitted by the laser is adjustable.

11. The method according to claim 2, wherein the marker is a light-absorbing marker arranged on a surface of an acoustic lens of a probe of the photoacoustic imaging system; or
the marker is melanin in a skin corresponding to the target tissue of a test object; or
the marker is a light-absorbing marker on a surface of a skin corresponding to the target tissue of a test object; or the marker is a light-absorbing marker added on the acoustic lens; or the marker is a light-absorbing marker added in an ultrasonic couplant gel, wherein the first absorption coefficient of the light-absorbing marker with respect to the first optical pulse is lower than an absorption coefficient of the target tissue to the first optical pulse; and the second absorption coefficient of the light-absorbing marker with respect to the second optical pulse is lower than an absorption coefficient of the target tissue to the second optical pulse.

12. The method according to claim 11, wherein a shape of the light-absorbing marker arranged on the surface of the acoustic lens of the probe of the photoacoustic imaging system comprises one of the following shapes: line, point, polygon, and irregular shape.

13. The method according to claim 2, wherein a wavelength of a light transmitted by the laser is adjustable.

14. A photoacoustic imaging system, comprising:
an ultrasonic probe;
a laser configured to transmit a first optical pulse and a second optical pulse to a target tissue, the first optical pulse having a first wavelength and the second optical pulse having a second wavelength;
a receiving circuit configured to control the ultrasonic probe to receive a first acoustic wave generated by the target tissue absorbing the first optical pulse to acquire a first photoacoustic signal, control the ultrasonic probe to receive a second acoustic wave generated by the target tissue absorbing the second optical pulse to acquire a second photoacoustic signal, control the ultrasonic probe to receive a third acoustic wave generated by the marker absorbing the first optical pulse to acquire a third photoacoustic signal, and receive a fourth acoustic wave generated by the marker absorbing the second optical pulse to acquire a fourth photoacoustic signal;
a memory configured to store executable program instructions;
a processor configured to execute the executable program instructions stored in the memory, so that the processor executes the method according to claim 2; and
a display configured to display visual information.

15. The system according to claim 14, wherein the marker is a light-absorbing marker arranged on a surface of an acoustic lens of a probe of the photoacoustic imaging system; or the marker is melanin in a skin corresponding to the target tissue of a test object; or the marker is a light-absorbing marker on a surface of a skin corresponding to the target tissue of a test object; or the marker is a light-absorbing marker added on the acoustic lens; or the marker is a light-absorbing marker added in an ultrasonic couplant gel.

16. The system according to claim 15, wherein the first absorption coefficient of the light-absorbing marker with respect to the first optical pulse is lower than an absorption coefficient of the target tissue to the first optical pulse; and the second absorption coefficient of the light-absorbing marker with respect to the second optical pulse is lower than an absorption coefficient of the target tissue to the second optical pulse.

17. The system according to claim 14, wherein acquiring a first brightness value of a region corresponding to at least part of the marker in the first photoacoustic image comprises:

acquiring pixel values of multiple pixels in the region corresponding to at least part of the marker in the first photoacoustic image; and determining the first brightness value based on the pixel values of multiple pixels, wherein the first brightness value comprises one of a mean value of the pixel values of multiple pixels, a median value of the pixel values of multiple pixels, and a pixel value corresponding to a peak value of a histogram of the pixel values of multiple pixels.

18. The system according to claim 14, wherein acquiring a second brightness value of the region corresponding to at least part of the marker in the second photoacoustic image comprises:

acquiring pixel values of multiple pixels in the region corresponding to at least part of the marker in the second photoacoustic image; and determining the second brightness value based on the pixel values of multiple pixels, wherein the second brightness value comprises a mean value of the pixel values of multiple pixels, a median value of the pixel values of multiple pixels, or a pixel value corresponding to a peak value of a histogram of the pixel values of multiple pixels.

19. The system according to claim 14, wherein correcting a signal intensity of the first photoacoustic signal based on the first brightness value together with a first absorption coefficient of the marker with respect to the first optical pulse and correcting a signal intensity of the second photoacoustic signal based on the second brightness value together with a second absorption coefficient of the marker with respect to the second optical pulse comprise:

dividing the signal intensity of the first photoacoustic signal by the first brightness value and then multiplying by the first absorption coefficient to acquire the corrected signal intensity of the first photoacoustic signal; and dividing the signal intensity of the second photoacoustic signal by the second brightness value and then multiplying by the second absorption coefficient to acquire the corrected signal intensity of the second photoacoustic signal.

20. The method according to claim 1, wherein the imaging wavelength range includes a wavelength of the first optical pulse and a wavelength of the second optical pulse.

* * * * *